(12) United States Patent
Abeyratne et al.

(10) Patent No.: US 11,864,880 B2
(45) Date of Patent: Jan. 9, 2024

(54) METHOD FOR ANALYSIS OF COUGH SOUNDS USING DISEASE SIGNATURES TO DIAGNOSE RESPIRATORY DISEASES

(71) Applicant: THE UNIVERSITY OF QUEENSLAND, Brisbane (AU)

(72) Inventors: Udantha Abeyratne, Brisbane (AU); Vinayak Swarnkar, Brisbane (AU)

(73) Assignee: THE UNIVERSITY OF QUEENSLAND, Brisbane (AU)

( * ) Notice: Subject to any disclaimer, the term of this patent is extended or adjusted under 35 U.S.C. 154(b) by 461 days.

(21) Appl. No.: 16/956,104

(22) PCT Filed: Dec. 20, 2018

(86) PCT No.: PCT/AU2018/051372
§ 371 (c)(1),
(2) Date: Jun. 19, 2020

(87) PCT Pub. No.: WO2019/119050
PCT Pub. Date: Jun. 27, 2019

(65) Prior Publication Data
US 2021/0076977 A1 Mar. 18, 2021

(30) Foreign Application Priority Data
Dec. 21, 2017 (AU) ................... 2017905129

(51) Int. Cl.
*G06K 9/00* (2022.01)
*A61B 5/08* (2006.01)
(Continued)

(52) U.S. Cl.
CPC .......... *A61B 5/0803* (2013.01); *A61B 5/0823* (2013.01); *A61B 5/7267* (2013.01);
(Continued)

(58) Field of Classification Search
CPC ... A61B 5/0803; A61B 5/0823; A61B 5/7267; A61B 7/003; G16H 50/30; G16H 50/20
See application file for complete search history.

(56) References Cited

U.S. PATENT DOCUMENTS

| | | | | | |
|---|---|---|---|---|---|
| 5,598,508 | A | * | 1/1997 | Goldman | A61B 5/7264 706/20 |
| 2009/0312660 | A1 | * | 12/2009 | Guarino | G16H 50/80 600/529 |

(Continued)

FOREIGN PATENT DOCUMENTS

| | | |
|---|---|---|
| EP | 3 231 368 | 10/2017 |
| WO | 2006/129098 | 12/2006 |

(Continued)

OTHER PUBLICATIONS

International Search Report for PCT/AU2018/051372 dated Mar. 22, 2019, 4 pages.
Written Opinion of the ISA for PCT/AU2018/051372 dated Mar. 22, 2019, 6 pages.

*Primary Examiner* — Avinash Yentrapati
(74) *Attorney, Agent, or Firm* — Nixon & Vanderhye PC

(57) ABSTRACT

A method for diagnosing one or more diseases of the respiratory tract for a patient including the steps of: acquiring cough sounds from the patient; processing the cough sounds to produce cough sound feature signals representing one or more cough sound features from the cough segments; obtaining one or more disease signatures based on the cough sound feature signals; and classifying the one or more disease signatures to deem the cough segments as indicative of one or more of said diseases; wherein the step of obtaining the one or more disease signatures based on the cough sound feature signals includes applying the cough sound features to each of one or more pre-trained disease signature decision machines, each said decision machine having been pre-trained to classify the cough sound features (Continued)

as corresponding to either a particular disease or to a non-disease state or as corresponding to first particular disease or a second particular disease different from the first particular disease.

28 Claims, 6 Drawing Sheets

(51) Int. Cl.
*G16H 50/30* (2018.01)
*G16H 50/20* (2018.01)
*A61B 5/00* (2006.01)
*A61B 7/00* (2006.01)

(52) U.S. Cl.
CPC ............. *A61B 7/003* (2013.01); *G16H 50/20* (2018.01); *G16H 50/30* (2018.01)

(56) References Cited

U.S. PATENT DOCUMENTS

| | | | |
|---|---|---|---|
| 2012/0071777 A1* | 3/2012 | MacAuslan | A61B 5/7282 600/529 |
| 2015/0073306 A1* | 3/2015 | Abeyratne | A61B 5/0823 600/586 |
| 2018/0021010 A1* | 1/2018 | Stamatopoulos | A61B 5/0205 600/484 |
| 2019/0080803 A1* | 3/2019 | Lotan | G16H 50/30 |
| 2019/0192047 A1* | 6/2019 | Stamatopoulos | G10L 25/66 |

FOREIGN PATENT DOCUMENTS

| | | | |
|---|---|---|---|
| WO | 2008/152433 | 12/2008 | |
| WO | 2013/142908 | 10/2013 | |
| WO | WO-2013142908 A1 * | 10/2013 | ........... A61B 5/0803 |

* cited by examiner

METHOD FOR ANALYSIS OF COUGH SOUNDS USING DISEASE SIGNATURES TO DIAGNOSE RESPIRATORY DISEASES

This application is the U.S. national phase of International Application No. PCT/AU2018/051372 filed Dec. 20, 2018 which designated the U.S. and claims priority to AU Patent Application No. 2017905129 filed Dec. 21, 2017, the entire contents of each of which are hereby incorporated by reference.

TECHNICAL FIELD

The present invention concerns methods and apparatus for assisting medical staff to diagnose and treat patients suffering from respiratory diseases.

BACKGROUND ART

Any references to methods, apparatus or documents of the prior art are not to be taken as constituting any evidence or admission that they formed, or form part of the common general knowledge.

In previous work by one or more of the same Inventors, which is the subject of international patent application PCT/AU2013/000323, hereby incorporated in its entirety by reference, patient respiratory tract sounds were recorded and from them cough sounds were identified. Features were extracted from the cough sounds to form test feature vectors which were then applied to pre-trained classifier, preferably a logistic regression model, in order to diagnose the presence of a respiratory dysfunction, such as pneumonia, in the patient.

Whilst the method for diagnosing a diseases state that is described in PCT/AU2013/000323 has worked well and has been successfully commercially implemented, nevertheless there is a need for improvement. For example it would be advantageous if a method were provided that was an improvement in that it could produce a more accurate diagnosis. It would also be preferable if the method could inject domain specific information into the diagnostic process. Furthermore, it would be desirable if the somewhat subjective nature of standard clinical diagnosis could be accommodated.

It is an object of the present invention to provide a method and apparatus for assisting in the diagnosis of a disease state of the respiratory tract.

SUMMARY OF THE INVENTION

According to a first aspect of the present invention there is provided a method for diagnosing one or more diseases of the respiratory tract for a patient including the steps of:
  acquiring cough sounds from the patient;
  processing the cough sounds to produce cough sound feature signals representing one or more cough sound features from the cough segments;
  obtaining one or more disease signatures based on the cough sound feature signals; and
  classifying the one or more disease signatures to deem the cough segments as indicative of one or more of said diseases;
  wherein the step of obtaining the one or more disease signatures based on the cough sound feature signals includes applying the cough sound features to each of one or more pre-trained disease signature decision machines, each said decision machine having been pre-trained to classify the cough sound features as corresponding to either a particular disease or to a non-disease state or as corresponding to first particular disease or a second particular disease different from the first particular disease.

In a preferred embodiment of the present invention the one or more disease signature machines each comprise a trained Logistic Regression Model (LRM).

Each trained Logistic Regression Model (LRM) may be trained using a reduced set of training features being features of the available set of training features that are determined to be significant to the LRM to thereby avoid overtraining of the LRM.

The training features may be determined to be ones of significance to the LRM by computing mean p-values for all training features and then selecting the features with mean p-values less than a threshold $P_{min}$. Further details of this process according to an embodiment of the present invention are set forth in Appendix F herein.

In this embodiment the independent variables for each LRM are values of the cough sound features and the output value from the LRM comprises a prediction probability of the cough indicating the first particular disease with reference to the second particular disease or with reference to a non-disease state.

Disease signatures may also be trained to generate scales associated with particular assessment or measurement outcomes used in respiratory medicine. Examples: Wheeze Severity Scores (WSS) by training a signature to separate low WSS vs high WSS; Low FEV1 vs high FEV1 as measured in spirometry; low FEV1/FVC vs high FEV1/FVC as measured in spirometry.

In another embodiment of the invention the one or more disease signature machines may include one or more trained neural networks. Other classifiers or models giving continuous outputs (e.g. generalized linear models, Hidden Markov Models etc.) can also be used as signal machines.

The method may further include applying clinical patient measurements, in addition to the cough features, as independent variables to the disease signature decision machines.

In one embodiment of the invention the step of classifying the one or more disease signatures to deem the cough segments as indicative of one or more of said diseases includes applying the one or more disease signatures to a single classifier that is trained to cover all disease groups.

In another embodiment of the invention the step of classifying the one or more disease signatures to deem the cough segments as indicative of one or more of said diseases includes applying the one or more disease signatures to a multiplicity of classifiers that are each trained to recognize a disease of interest.

In a preferred embodiment the classifiers are each trained to recognise one of the following diseases: Bronchiolitis ($S_{Bo}$); Croup ($S_C$); Asthma/RAD ($S_A$); Pneumonia ($S_P$); Lower respiratory tract diseases ($S_{LRTD}$); Primary URTI ($S_U$).

Preferably d disease signatures are produced by the step of obtaining one or more disease signatures based on the cough sound feature signals and correspondingly the Artificial Neural Network (ANN) has a d-dimensional input layer with one input neuron corresponding to each of the disease signatures.

In a preferred embodiment of the invention the ANN has a k-dimensional output layer wherein each neuron in the output layer outputs a probability corresponding to a disease In a preferred embodiment of the invention the step of classifying the one or more disease signatures includes compiling a compound effective probability measure y compiling a compound effective probability measure $P_Q'$ as:

$$P_Q' = P_Q(1-P_z)$$

where $P_Q$ comprises an indicator of the probability of the patient belonging to disease Q and $P_z$ to disease Z. Thus the product $P_Q(1-P_Z)$ indicates the probability of the compound event that the patient belongs to disease Q AND does not belong to disease Z.

The method may include computing a cough index for each of the target diseases wherein the cough index of a patient for a target disease is computed as the ratio of coughs of the patient classified as indicative of the target disease to the total number of coughs analysed for said patient.

The method may further include applying specific therapy, for example a treatment known to be efficacious to the patient based upon the particular disease diagnosed.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows.

DETAILED DESCRIPTION OF PREFERRED EMBODIMENTS

Figure 1:
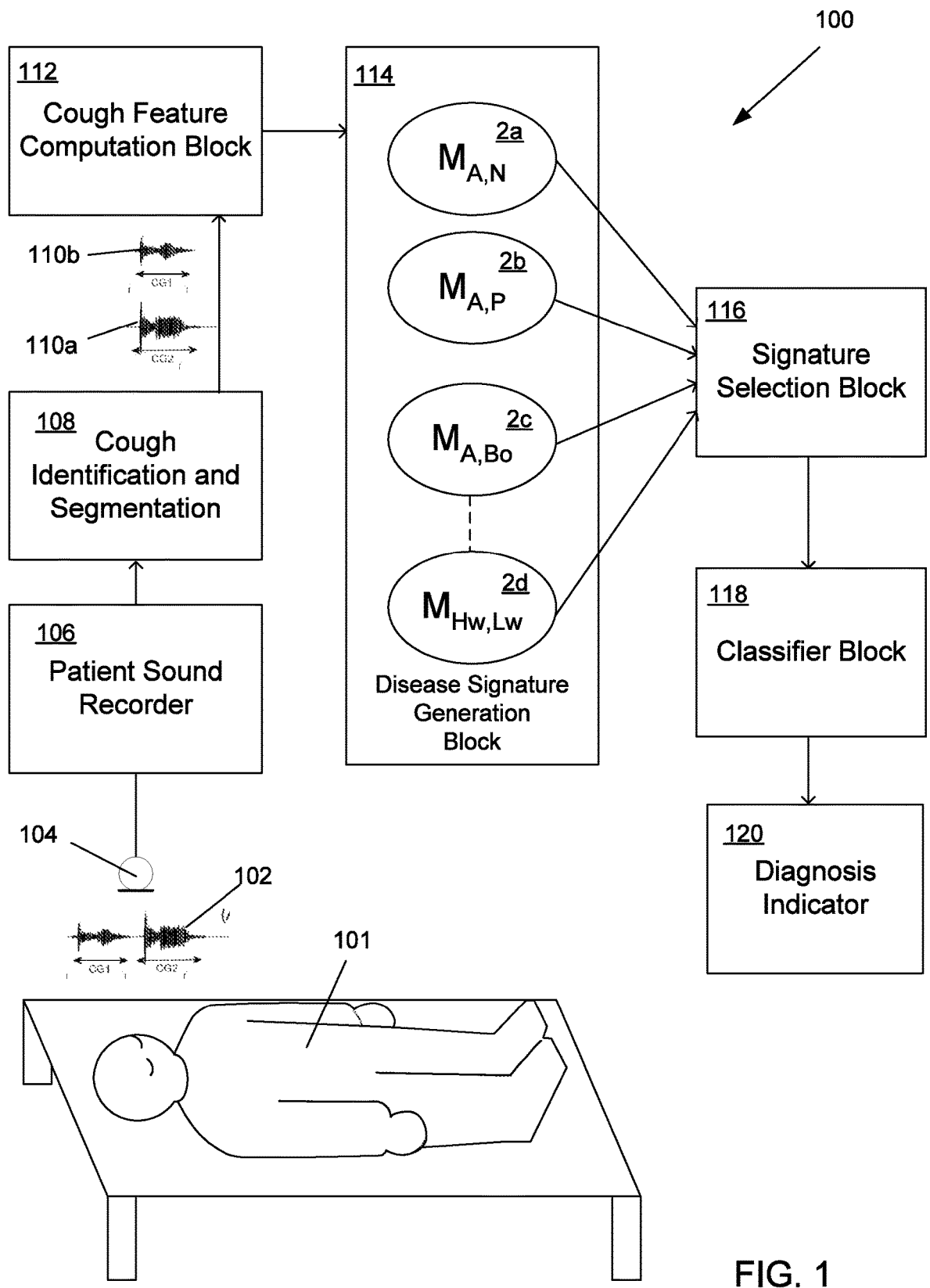
FIG. 1 Is a flowchart of a preferred diagnostic method according to a first embodiment of the present invention.

FIG. 1 depicts flowchart 100 of a method according to a preferred embodiment of the present invention. The method 100 includes four major processing boxes or blocks as follows: Cough Feature Computation Block 112, Disease-Signature Generation 114, Signature Selection 116 and Signature Classifier Block 118. Each of these blocks can be implemented to provide an apparatus, for example by using a specially programmed computer to implement the various functionalities that will be described herein. Alternatively, the various processing blocks can also be implemented using custom electronic integrated circuits chips and discrete logic. More particularly, some of the blocks, such as classifier block 118 implement Artificial Neural Networks (ANN) and may be implemented using dedicated ANN integrated circuits such as the Synapse chip by IBM or the Zeroth processor by Qualcomm or their equivalents.

Patient sound 102 is recorded at box 106 from a patient 101 via microphone 104. The audio recording is passed to a cough identification and segmentation block 108 which processes the audio recording and automatically segments it into cough sounds e.g. CG1 110a and CG2 110b. The cough sounds 110a, 110b, which consist of digitized signals, e.g. electronic MP3 file segments, are transferred to the cough feature computation block 114. The cough feature computation block 114 is arranged to process each of the cough sounds to extract cough feature values in the form of signals, e.g. electrical signals transmitted on circuit board or integrated circuit conductors, which represent to what degree each cough possesses each of one of a number of characterising features, that will be described. The output signals from the cough feature computation block 112 are processed by signature generation block 114. The signature generation block 114 comprises a plurality of pre-trained decision machines 2a to 2n, preferably trained logistic regression machines, which have each been pre-trained to classify the cough feature signals as indicative of a first or a second particular disease (or group of diseases). One of the pre-trained decision machines 2a to 2n may also have been trained to classify the cough feature signals as indicative of a particular disease or as normal (i.e. non-diseased).

The signature selection block 116 receives signals output from the disease signature generation block 114 and is arranged to identify from them a set of signatures that will provide the best diagnostic outcomes on a training/validation set of data at the output of the classifier block 118. The signature selection block 116 is arranged to take into account multiple factors as follows:

(i) the ability to provide good training and validation performance at the individual signature generation process, (ii) domain specific knowledge (for instance, if the target of the final classifier is to diagnose asthma/RAD, a WSS signature is expected to be useful since wheezing is a strong indicator of asthma/RAD. If the classifier has to diagnose pneumonia, a pneumonia vs bronchiolitis signature may be indicated because these are known to present diagnostic dilemmas in clinical practice etc.), (iii) based on a search process on signatures to maximise diagnostic performance at the classifier output on the training/validation set.

The output values from the selected signature selection block 116 are passed to classifier block 118 which is preferably comprised of a plurality of pre-trained neural networks, each of which is pre-trained to classify the outputs of the selected signature generators as one or other of a number of predetermined diseases.

Diagnosis indication block 120 is responsive to the classifier block 118 and presents indications on disease diagnosis that can be used by a clinician to confirm a disease diagnosis and to provide appropriate therapy to the patient. The output box 120 involves the presentation, for example on a visual electronic display, of a diagnostic indication of a single disease or a number of diseases to a clinician or other career for the patient who may then apply specific therapy, for example a treatment known to be efficacious to the patient based upon the particular disease diagnosed.

Further details will now be provided in the following discussion.

Cough Feature Computation Box 112

At box 112 the segments from the patient recordings that have been identified as containing cough events are applied to a processing block that is arranged to extract mathematical features from each cough event in the manner described in PCT/AU2013/000323.

In addition, and according to the preferred embodiment of the invention, Cough Feature Computation Block 112 is also arranged to extract a cepstral coefficient based on Higher-Order-Spectra slices, inspired by the Mel-Frequency Cepstral Coefficents (MFCC) coefficients. The new coefficients are referred to herein as the BFCC (Bispectral Frequency Cepstral Coefficients) and are described in further detail in Appendix B (i) herein.

The Cough Feature Computation Box is arranged to carry out the following process in use is as follows:
(i) Let x denotes a discrete time sound signal from an arbitrary cough event.
(ii) Segment x into, for example, three equal sized non-overlapping sub-segments. The objective target is to capture the variation of mathematical features within a single cough. Let $x_i$ represents the $i^{th}$ sub-segment of x, where i=1, 2, 3.
From each sub-segments $x_i$ compute the following features: the 8 Bispectrum coefficients (BC), a Non-Gaussianity score (NGS), the first four formant frequencies (FF), a log energy (Log E), a zero crossing (ZCR), a kurtosis (Kurt), 31 Mel-frequency cepstral coefficients (MFCC), a Shannon Entropy (ShE).
(iii) In addition, compute 13 wavelet features using the whole cough event data [2]. For a brief description of each cough feature please see appendix B.
(iv) A total of $C_f$=157 features are extracted from each cough event.

Disease Signature Generation Box 114

In the previous work that is the subject of PCT/AU2013/000323 patients were directly classified by training a logistic regression model on the features sets computed in Box 112.

In contrast to the approach taken in PCT/AU2013/000323 a preferred embodiment of the present invention involves a new procedure that has been conceived and which is referred to herein as "Signature Generation", with several purposes in mind: (a) as a method to inject domain specific information to the diagnostic process, (b) as a method of accommodating the subjective nature of the standard clinical diagnosis, (c) as a way of producing a more accurate diagnosis.

Signature Generation, which is carried out at box 114, involves mapping the input features from the Cough Feature Computation Block 112 to a set of axes, which are represented in a digital memory, that vary continuously between 0 and 1 and define a space in which a classifier can better diagnose individual diseases. Each of these axes are referred to as a signature. Every patient provides a response along each of the axes (signatures) and the collection of response values for each signature for each patient are then sent to the classifier block 118 which produces a diagnosis that is presented in diagnosis indication block 120. As will be explained, the axes (signatures) embed domain-specific knowledge.

In one embodiment, input features to box 114 from box 112 can be converted to signatures by training Logistic Regression models (LRMs). For instance, signature axes can be achieved by training a collection of models such as {(bronchiolitis vs normal), (croup vs normal), (bronchiolitis vs croup), (bronchiolitis vs all disease), (croup vs A/RAD) . . . etc. etc}. Each model provides one signature. The actual signatures used depend on the disease group that requires diagnosis. Signatures can also be built with models such as (high wheeze severity scores WSS=5, 6, 7 vs low wheeze severity scores WSS=0, 1, 2) and clinical signs based models where map clinical signs are mapped (e.g. fever, runny nose) to a continuous variable between 0 and 1. Any other classifier that maps input to a continuous decision variable, e.g. a neural network, can be used in generating the Signature Block as an alternative to an LRM.

The Logistic-Regression (LR) model is a generalized linear model, which uses several independent variables to estimate the probability of a categorical event. The relevant independent variables are the mathematical features computed from the cough events and categorical event are the disease subgroups. So in the above example, a LR model can be trained to predict the probability of a cough belonging to Bronchiolitis disease with reference to Croup disease. The LR model is derived using a regression function to estimate the probability Y given the independent features as follows:

$$\text{Prob}(Y) = \frac{e^z}{e^z + 1} \tag{1}$$

$$z = \beta_0 + \beta_1 \cdot q_1 + \beta_2 q_2 + \ldots + \beta_{n-1} q_F \tag{2}$$

In (2), $\beta_0$ is called the intercept and $\beta_1$, $\beta_2$ and so on are called the regression coefficients of independent variables, $q_1, q_2, \ldots q_F$, representing features.

In order to produce the required LR models $2a, \ldots, 2n$ of the Disease Signature Generation block 114, it is necessary to train them using acquired cough sounds. The LRM models $2a, \ldots, 2n$ are trained guided by their ability to correctly classify disease or measurement classes on relevant patient sub-groups. Once trained, they are used to generate continuous valued probability output signals between (0, 1) for all patients that require a diagnosis.

Cough Sound Acquisition

Cough sounds were recorded from two clinical sites, Joondalup Health Campus (JHC) and Princess Margaret Hospital (PMH), both in Perth, Western Australia. Patient population included children aged between 0-12 years and suspected of respiratory illnesses such as pneumonia, asthma/RAD (Reactive Airway Disease), bronchiolitis, croup and upper respiratory tract infection (URTI). The human ethics committees of The University of Queensland, Joondalup Health Campus and Princess Margaret Hospital had approved the study protocols and the patient recruitment procedure.

Patients fulfilling the inclusion criteria (presenting with cough, wheeze, shortness of breath, stridor, URTI) and not satisfying the exclusion criteria (requiring respiratory support, no consent given) were recruited to the study Healthy subjects, defined as children who did not have any symptom of respiratory disease at the time of measurement, were also recruited.

Cough sounds were recorded (see box 106 of FIG. 1) using an Apple iPhone 6s. Sound data were recorded at a sampling rate of $f_s$=44.1 k samples/s at a bit depth of 16-bits per sample. The smartphone recorder was placed approximately 50 cm away from mouth and at an angle of approximately 45°.

Database & Experimental Design

The database that was used to train the various models required to implement the apparatus of FIG. 1 consists of cough recordings and detailed clinical diagnostic information on each patient including the final diagnosis, clinical examination findings and laboratory as well as imaging outcomes. Demographic information was also available in a patient de-identified format.

Diagnostic Groups (case Definitions used in diagnosing diseases are given in Appendix A).

Normal Group (Nr): healthy volunteers with no discernible respiratory illness at the time of measurement.

Primary URTI Group (U): patients with upper respiratory tract infections (URTI) alone, without medically discernible lower respiratory tract involvement or other respiratory disease at the time of measurement.

Croup Group (C): patients with a diagnostic classification of croup alone or with the co-morbidity of URTI.

Asthma/Reactive airway disease Group (A): patients with a diagnostic classification of asthma or reactive airway disease, with or without URTI as co-morbidity.

Clinical Pneumonia Group (P): patients with a diagnostic classification of clinical pneumonia with or without URTI as co-morbidity.

Bronchiolitis Group (Bo): patients with a diagnostic classification of bronchiolitis with or without URTI as co-morbidity.

Bronchitis Group (Bc): patients with a diagnostic classification of bronchitis with or without URTI as co-morbidity.

The overall subjects were divided into two mutually exclusive sets to train, validate and test the classifier models. The two mutually exclusive sets were: (1) the Training-Validation Set (TrV), and (2) the Prospective Testing Set (PT). Each subject belonged to just one set only. Subjects with diagnostic uncertainties (as indicated by the clinical team) and disease co-morbidities except URTI were excluded from the TrV.

The Training-Validation Set TrV is used to train and validate the models following a Leave-One-Out-Validation (LOOV) or K-fold cross validation techniques. The LOOV method involves using data from all the patients except one to train the model and cough events from the remaining patient to validate the model. This process was systematically repeated such that each patient in TrV was used to validate a model exactly one time. In the K-fold cross validation, the original sample is randomly partitioned into K equal sized subsamples. A single subsample is retained as the validation data for testing the model. The remaining (K−1) samples will be used to train models. The process will be repeated K times until all the data in the TrV is used once in testing the models. Note that the LOOV is a special case of K-fold cross validation method with K set to the total number (N) of the data in the set TrV.

Table 1 (overpage) lists the different LR models $2a, \ldots, 2n$ trained in the Disease Signature Generation block 114 of FIG. 1.

TABLE 1

Figure 2:
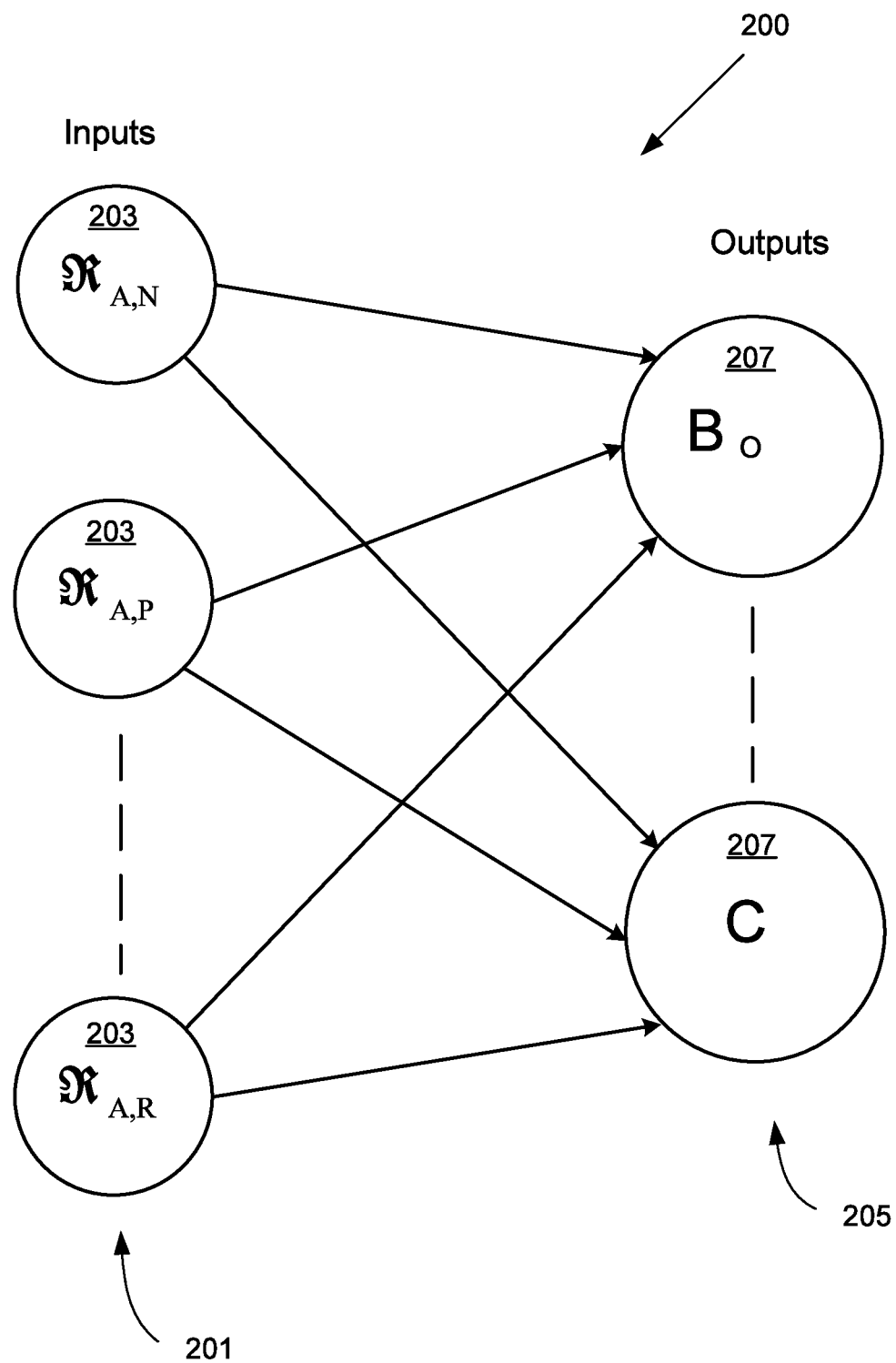
FIG. 2 Depicts an Artificial Neural Network architecture with d-dimensional input layer (inputs from signature block in Figure B) and k-dimensional output layers. Each neuron in the output layer corresponds to a disease subgroup.

List of Signature Generating models trained in the signature block of FIG. 2 in a LOOV embodiment.

| | Signatures | Success | LOOV Models $j = 1, 2, \ldots N_k$ | Particular Model selected after Step 3 |
|---|---|---|---|---|
| 1 | Asthma Vs Pneumonia | Success is defined as correctly picking Asthma class | $\{M_{A,P}\}_j$ | $\Re_{A,P}$ |
| 2 | Asthma Vs Bronchiolitis | | $\{M_{A,Bo}\}_j$ | $\Re_{A,Bo}$ |
| 3 | Asthma Vs Bronchitis | | $\{M_{A,Bc}\}_j$ | $\Re_{A,Bc}$ |
| 4 | Asthma Vs Croup | | $\{M_{A,C}\}_j$ | $\Re_{A,C}$ |
| 5 | Asthma Vs URTI | | $\{M_{A,U}\}_j$ | $\Re_{A,U}$ |
| 6 | Asthma Vs Rest of diseases | | $\{M_{A,R}\}_j$ | $\Re_{A,R}$ |
| 7 | Asthma Vs Normal | | $\{M_{A,Nr}\}_j$ | $\Re_{A,Nr}$ |
| 8 | Pneumonia Vs Bronchiolitis | Success is defined as correctly picking Pneumonia class | $\{M_{P,Bo}\}_j$ | $\Re_{P,Bo}$ |
| 9 | Pneumonia Vs Bronchitis | | $\{M_{P,Bc}\}_j$ | $\Re_{P,Bc}$ |
| 10 | Pneumonia Vs Croup | | $\{M_{P,C}\}_j$ | $\Re_{P,C}$ |
| 11 | Pneumonia Vs URTI | | $\{M_{P,U}\}_j$ | $\Re_{P,U}$ |
| 12 | Pneumonia Vs Rest of diseases | | $\{M_{P,R}\}_j$ | $\Re_{P,R}$ |
| 13 | Pneumonia Vs Normal | | $\{M_{P,Nr}\}_j$ | $\Re_{P,Nr}$ |
| 14 | Bronchiolitis Vs Bronchitis | Success is defined as correctly picking Bronchiolitis class | $\{M_{Bo,Bc}\}_j$ | $\Re_{Bo,Bc}$ |
| 15 | Bronchiolitis Vs Croup | | $\{M_{Bo,C}\}_j$ | $\Re_{Bo,C}$ |
| 16 | Bronchiolitis Vs URTI | | $\{M_{Bo,U}\}_j$ | $\Re_{Bo,U}$ |
| 17 | Bronchiolitis Vs Rest of diseases | | $\{M_{Bo,R}\}_j$ | $\Re_{Bo,R}$ |
| 18 | Bronchiolitis Vs Normal | | $\{M_{Bo,Nr}\}_j$ | $\Re_{Bo,Nr}$ |
| 19 | Bronchitis Vs Croup | Success is defined as correctly picking Bronchitis class | $\{M_{Bc,C}\}_j$ | $\Re_{Bc,C}$ |
| 20 | Bronchitis Vs URTI | | $\{M_{Bc,U}\}_j$ | $\Re_{Bc,U}$ |
| 21 | Bronchitis Vs Rest of diseases | | $\{M_{BC,R}\}_j$ | $\Re_{BC,R}$ |
| 22 | Bronchitis Vs Normal | | $\{M_{BC,Nr}\}_j$ | $\Re_{BC,Nr}$ |
| 23 | Croup Vs URTI | Success is defined as correctly picking Croup class | $\{M_{C,U}\}_j$ | $\Re_{C,U}$ |
| 24 | Croup Vs Rest of diseases | | $\{M_{C,R}\}_j$ | $\Re_{C,R}$ |
| 25 | Croup Vs Normal | | $\{M_{C,Nr}\}_j$ | $\Re_{C,Nr}$ |
| 26 | High Wheeze Score (HWS) Vs Low Wheeze Score (LWS) | Success is defined as correctly picking Subjects with High Wheeze Score | $\{M_{Hw,Lw}\}_j$ | $\Re_{Hw,Lw}$ |

The data in the TrV dataset was used to train and validate all the LR models listed in Table 1.

In the simplest form, only cough-based features are used to train LR models. However the Inventors have recognized the existence of some simple clinical measurements that may be used to improve performance of LR models at no-extra cost and minimal complexity. Inspired by this the Inventors appended cough based features with simple clinical features and trained a $2^{nd}$ set of LR models list in table 1. Table 2 shows the simple clinical features appended with cough based features.

TABLE 2

'✓' indicates the inclusion of that feature in model design. Clinical signs were taken from the patient history as reported by parent during the clinical examination.

| Features Combination | Age (in months) | Gender | History of Fever | History of Runny Nose | History of Hoarse Voice | History of Wheeze | Cough Feature (#157) |
|---|---|---|---|---|---|---|---|
| Cough Only | | | | | | | ✓ |
| Cough, Simple Clinical Feature | ✓ | ✓ | ✓ | ✓ | ✓ | ✓ | ✓ |

Feature Selection

Feature selection is a technique of selecting relevant features for designing an optimal signature model. For instance, in building an LR model as a signature using the TrV set, p-value is computed for each input feature capturing how significant a particular feature is to the model. Important features have low p-value. This property of LR model was used over the entire TrV set to select a reasonable combination of features. Once the subset of significant feature was known, it was used to re-train LR models based on the LOOV (K-fold) training/validation on TrV dataset. More details of the feature selection process can be found in the previously referenced earlier PCT application and in Abeyratne, U. R., et al., Cough sound analysis can rapidly diagnose childhood pneumonia. Annals of biomedical engineering, 2013. 41(11): p. 2448-2462.

Selecting a Good LR Model

The LOOV training/validation process results in $N_k$ number of LR models, where $N_k$ is the number of patients in the TrV set. The value of $N_k$ will vary for different LR model listed in table 1 due to the different numbers of patients in different disease groups in the TrV set. From the $N_k$ LR models, one of the best models was selected based on the k-mean clustering algorithm. More details on using k-mean clustering algorithm for model selection can be found in [1].

Let $\mathfrak{R}_{c,j}$ represent a selected signature based on an LR model j trained using cough only features and $\mathfrak{R}_{cf,j}$ represent a selected LR model trained using cough plus simple clinical features. Once the LR model is selected it is run through all the patients in the TrV dataset to generate the disease signatures.

These signatures provide 'responses' $\rho_{c,ij}=\mathfrak{R}_{c,j}(x_i)$ and $\rho_{cf,ij}=\mathfrak{R}_{cf,j}(x_i)$ of a given patient i against all hypotheses tested via the different signature values. The vector $x_i$ represents the collection of information such as cough sounds and clinical signs on the $i^{th}$ patient, required by the models $\mathfrak{R}_{c,j}$ and $\mathfrak{R}_{cf,j}$.

As an example, if a patient being tested has bronchiolitis, his/her response against a model such as {bronchiolitis vs all other diseases} should give a strong value closer to 1 ('full response'), whereas {A/RAD vs all other diseases} should give a lower response ('partial response'). However, the patient will give a particular response against each signature axis (LRM model), and the vector $V_{i,c}$ and $V_{i,cf}$ representing the collection of such responses for each patient 'i' will characterise the disease the patient is suffering from.

$$V_{i,c}=[\{\rho_{c,ij}\}|j\text{---all selected signatures(LRM models)}] \quad (3)$$

$$V_{i,cf}=[\{\rho_{c,ij}\}|j\text{=all selected signatures(LRM models)}] \quad (4)$$

Not all models $2a, \ldots, 2n$ available in the Signal Generator Block 114 are necessarily used in the final Signature Classifier Block 118. The choice of signatures is made in the signature selection block 116 which is arranged to take into account domain-specific knowledge and observations on how a particular signature is contributing to the final disease diagnostic performance as well as information redundancy among signatures. Table 1 entries provide a preferred list of such signatures chosen from a larger collection.

The Classifier Block 118

The function of Classifier Block 118 is to use the signatures $V_{i,c}$ and $V_{i,cf}$ provided by the Signal Generator Block 114 and label the likelihood of each cough recorded from each patient in belonging to a particular disease group. Then, an overall diagnostic decision is made on a per patient basis using several different methods. Multiple Classifier Blocks can be built to cover the disease groups of interest or to build a single classifier to cover all disease groups. Any classifier can be used in the Signature Classifier Block 118, but in a preferred embodiment, the Softmax Artificial Neural Network layer (Softmax ANN) was used as the classifier.

FIG. 2 shows a typical structure 200 of a soft-max ANN as used in block 118 of FIG. 1. For training and validation of ANN data from the TrV dataset was used and followed LOOV (or K-Fold) cross-validation process. The benefit of using a soft-max function is that, value of each neuron ranges between 0 and 1 and the sum of all the neurons in the output layer is 1. This makes it a useful function to model and predict probabilities of the disease subgroups. For instance, if it is desired to build the model to diagnose disease Q and it is known that disease Z appears as a confounder disease (for instance with some symptom overlaps), the diagnostic performance can be improved by compiling a compound effective probability measure $P_Q'$ as:

$$P_Q'=P_Q(1-P_Z) \quad (5)$$

where $P_Q$ can be treated as an indicator of the probability of the patient belonging to disease Q and Pz to disease Z. Thus the product $P_Q(1-P_Z)$ indicates the probability of the compound event that the patient {belongs to disease Q AND does not belong to disease Z).

The ANN depicted in FIG. 2 shows an Artificial Neural Network architecture with d-dimensional input layer 201 comprised of neurons 203 (inputs being received from signature block 114 in FIG. 1) and k-dimensional output layer 205. Each neuron 207 in the output layer 203 corresponds to a disease subgroup.

In a preferred embodiment, of the invention five different soft-max ANN models were trained to identify disease subgroups: Bronchiolitis, Croup, Asthma/RAD, Pneumonia and Lower respiratory track disease (LRTD). Details of these disease specific soft-max ANN are provided below.

1. Soft-max ANN for Bronchiolitis ($S_{Bo}$): In this soft-max ANN model Bronchiolitis centred signatures were used. The signatory LR models used to train ANN were $\{\mathfrak{R}_{Bo,R}, \mathfrak{R}_{A,Bo}, \mathfrak{R}_{P,Bo}, \mathfrak{R}_{Bo,Bc}, \mathfrak{R}_{Bo,C}, \mathfrak{R}_{Bo,U}, \mathfrak{R}_{Hw,Lw}\}$. At the output layer dimension of the k was set to 6 neurons with each neuron corresponding to one disease subgroups, Bronchiolitis, Asthma/RAD, Pneumonia, Bronchitis, pURTI, Croup. In eq. (5) $P_Q$ is the output of the Bronchiolitis neuron and $P_Z$ is the output of the RAD neuron.

2. Soft-max ANN for Croup ($S_C$): In this ANN model Croup centred signatures were used. The signatory LR models used were $\{R_{C,R}, \Re_{A,C}, \Re_{P,C}, \Re_{Bo,C}, \Re_{Bc,C}, \Re_{C,U}\}$. At the output layer dimension of the k was set to 6 neurons with each neuron corresponding to one disease subgroups, Bronchiolitis, Asthma/RAD, Pneumonia, Bronchitis, pURTI, Croup. In eq. (5) $P_Q$ is the output of the Croup neuron and $P_Z$ is the output of the pURTI neuron.

3. Soft-max ANN for Asthma/RAD ($S_A$): In this ANN model Asthma/RAD centred signatures were used. The signatory LR models used were $\{\Re_{A,R}, \Re_{A,C}, \Re_{A,P}, \Re_{A,Bo}, \Re_{A,Bc}, \Re_{A,U}, \Re_{Hw,Lw}\}$. At the output layer dimension of the k was set to 6 neurons with each neuron corresponding to one disease subgroups, Bronchiolitis, Asthma/RAD, Pneumonia, Bronchitis, pURTI, Croup. In eq. (5) $P_Q$ is the output of the Asthma/RAD neuron and $P_Z$ is the output of the pURTI neuron.

4. Soft-max ANN for Pneumonia ($S_P$): In Pneumonia, soft-max ANN model the signatory LR models used were $\{\Re_{A,P}, \Re_{A,Bo}, \Re_{A,C}, \Re_{P,R}, \Re_{P,U}, \Re_{P,C}, \Re_{P,Bo}, \Re_{P,Bc}, \Re_{Bo,R}, \Re_{C,R}, \Re_{Hw,Lw}\}$. At the output layer dimension of the k was set to 4 neurons; one neuron each for Bronchiolitis, Pneumonia & Croup and one neuron for diseases Asthma/RAD, Bronchitis, pURTI. In eq. (5) $P_Q$ is the output of the Pneumonia neuron and $P_Z$ is the output of the neuron for Asthma/RAD, Bronchitis, pURTI diseases.

5. Soft-max ANN for Lower respiratory tract diseases ($S_{LRTD}$): The Lower respiratory tract diseases (LRTD) is an umbrella term used to represent diseases which have lower respiratory tract involvement. LRTD subgroup combined the patients from Pneumonia, Asthma/RAD, Bronchiolitis and Bronchitis diseases. The LRTD soft-ANN model was trained to identify LRTD diseases from croup and pURTI. In this ANN LRTD centred signatures were used. The signatory LR models used were $\{\Re_{A,U}, \Re_{A,C}, \Re_{P,C}, \Re_{P,U}, \Re_{Bo,U}, \Re_{Bo,C}, \Re_{C,R}, \Re_{C,U}, \Re_{A,N}, \Re_{P,N}, \Re_{Bo,N}, \Re_{Bc,N}, \Re_{Hw,Lw}\}$. At the output layer dimension of the k was set to 3 neurons; one neuron each for URTI & Croup and one neuron for LRTD disease group. In eq. (5) $P_Q$ is the output of the LRTD neuron and $P_Z$ is the output of the neuron for pURTI.

6. Soft-max ANN for primary URTI ($S_U$): In this ANN model pURTI centred signatures were used. The signatory LR models used were $\{\Re_{A,U}, \Re_{P,U}, \Re_{Bo,R}, \Re_{Bo,U}, \Re_{Bc,U}, \Re_{Hw,Lw}, \Re_{P,Nr}, \Re_{U,Nr}\}$. At the output layer dimension of the k was set to 6 neurons with each neuron corresponding to one disease subgroups, Bronchiolitis, Asthma/RAD, Pneumonia, Bronchitis, pURTI, Croup. In eq. (5) $P_Q$ is the output of the pURTI neuron and $P_Z$ is the output of the Pneumonia neuron.

For training cough only soft-max ANN LR signature models were used developed using cough features only. For training cough plus simple clinical features soft-max ANN LR signature models were used developed using cough features only and/or cough plus simple clinical features.

Selecting a Preferred Soft-Max ANN Model

The LOOV cross-validation process will results in N number of soft-max models. Where N is the number of patient in TrV dataset. From the N models, the Inventors selected one of the best models again following the k-mean clustering algorithm. More details on using k-mean clustering algorithm for model selection can be found in [1]. Let $S^s$ represent the selected soft-max ANN and $\lambda^s$ be the corresponding probability decision threshold for a specific disease subgroup. Once $S^s$ is chosen, then fix all the parameters of the model and completely terminate the training process. The model $S^s$ is then used as the best model for further testing. A similar approach was used in the K-fold cross validation approach.

Other factors the Inventors explored in training the soft-max ANN is the size of the network, training epochs, training rates, stopping criteria and the difference between training and validation errors. These factors were explored with a view towards minimizing overlearning for the data set we had access to and maximizing the generalization to a statistically similar previously unseen population.

The following describes several preferred embodiments of the methodology that was used to arrive at a diagnostic decision on each patient.

i). Cough Index and Patient Based Classification

In this approach the outputs of the classifier (e.g. a softmax ANN) directly (e.g. $P_Q$, $P_Z$ etc.) or a probability compounded measure such as $P_Q'$ was processed. The first target is to test each cough given by a patient against the targeted disease class (e.g. bronchiolitis) and label each cough as either a csuccess=1' or a failure=0'. For instance, if the final target were to test against bronchiolitis, each cough was labelled as either bronchiolitic (success, indicated by a label of 1) or non-bronchiolitic (failure, indicated by a label of 0). To select the optimal decision threshold $\lambda$ (i.e. the cough under test belongs to target disease (success, 1) if the test statistic$\geq \lambda$) then the Receiver-Operating Curve (ROC) analysis was used on the TrV set.

A cough index was then computed for each of the target diseases as follows. Let $C_T$ be the total number of coughs analysed from a patient i and $C_S$ is the number of coughs that were labelled as 'success' by a soft-max ANN model. Then the cough index $CI_{i,j}$ of a patient i for a target disease subgroup j is computed as: $CI_{i,j} = C_S/C_T$.

ii). Classification Based on Deeper Learning Strategies

The raw output of the softmax layer (which is a continuously varying real number between 0 and 1) can be further processed in the spirit of deep leaning approaches. Some preferred embodiments are given below:

a) Raw outputs of the Softmax ANN of block 118 3 may be fed to another classifier such as a neural network which will simultaneously receive inputs from other similar networks trained with different philosophies. For instance the other network can be based entirely on clinical signs parents can easily observe and report to a clinician. The clinical-signs network can have an architecture parallel to the Disease Signature Generation block 114 of FIG. 1, or a simpler version such as a set of selected LRM classifier (or a ANN classifier etc.) mapping clinical signs to desired disease groups.

b) The LRM based signature generator models 2a, . . . , 2n of block 114 of FIG. 1 can be replaced by other classifiers such as ANN layers making the whole network ANN based, and follow the philosophy of deep learning networks. The Inventors have built and tested such models. Clinical-signs models can be incorporated as above.

In one preferred embodiment, the Inventors trained a deep neural network using the encoder approach.

The final classifier itself was a neural network with one neuron representing each of the disease classes of interest.

D. Testing the Process

In this section, we explore the performance of the final diagnostic models on a prospective data set. Prior to using the prospective data set we completely freeze our diagnostic models and no further training or parameter adjustment or protocol changes would be allowed.

Results

A. Dataset

Table 3 sets out the details of the subject population used in this study. For this work we used cough sound data from a total of N=1151 subjects (982 patient and 169 normal) to develop, validate and test our models. These patients were separated into two non-overlapping datasets, (1) the Training-Validation set (TrV), and (2) the Prospective Testing set (PT). Patients were assigned to each sets based on the order of presentation to the hospital.

TABLE 3

Details of the total subject population used in the study.

|  | Total subjects | | Training Validation Dataset | | Prospective testing dataset | |
| --- | --- | --- | --- | --- | --- | --- |
|  | JHC | PMH | JHC | PMH | JHC | PMH |
| Patient | 730 | 252 | 600 | 252 | 130 | 1 |
| Normal | 143 | 26 | 134 | 25 | 9 | 0 |

Training-Validation dataset: For model training and validation we froze our dataset once we had a total of 1011 subjects (852 patient & 159 normal) recruited from two sites; 600 patient and 134 normal Prospective Testing dataset: There were total of 130 patients all from recording site JHC and 10 normal subjects recording (9 from JHC and 1 from PMH).

Following the clinical adjudication and in consultation with the clinical team the subjects in the datasets were classified into a range of diagnostic subgroups: Normal Group (Nr), Primary URTI Group (U), Croup Group (C), Asthma/Reactive airway disease Group (A), Clinical Pneumonia Group (P), Bronchiolitis Group (Bo), Bronchitis Group (Bc).

B. Performance of the Signature Models on the Training-Validation Dataset.

Out of 1011 subjects 725 subjects (602 patients 123 normal subject) were finally used for model training and validation.

Table 4

Diagnostic disease subgroups.

|  | Disease subgroups | Training Validation Dataset (TrV) |
| --- | --- | --- |
| 1 | Normal Group (Nr) | 123 |
| 2 | Asthma Group (A) | 234 |
| 3 | Pneumonia Group (P) | 122 |
| 4 | Bronchiolitis Group (Bo) | 101 |
| 5 | Bronchitis Group (Bc) | 35 |
| 6 | Croup Group (C) | 57 |
| 7 | URTI Group (U) | 53 |
|  | Total | 725 |

Table 4 shows the number of patients in each disease subgroups used for training-validating models.

LR model for Normal vs Disease: At first we explored the performance of the LR signatory models in classifying coughs from normal subjects and any disease subgroup subjects. Table 5 shows the leave-one-out validation results of this exploration.

TABLE 5

Leave-one-out validation results in classifying normal coughs from disease coughs using signatory LR models.

| LOOV Models | Cough features only | | | Cough plus simple clinical features | | |
| --- | --- | --- | --- | --- | --- | --- |
| $j = 1, 2, \ldots N_k$ | Sensitivity | Specificity | Accuracy | Sensitivity | Specificity | Accuracy |
| Using all the features | | | | | | |
| $\{M_{A, Nr}\}_j$ | 83.30 | 78.71 | 82.00 | 97.66 | 94.46 | 96.75 |
| $\{M_{P, Nr}\}_j$ | 49.15 | 87.17 | 65.02 | 95.77 | 93.61 | 94.87 |
| $\{M_{Bo, Nr}\}_j$ | 82.73 | 89.90 | 85.94 | 97.98 | 96.96 | 97.53 |
| $\{M_{BC, Nr}\}_j$ | 63.33 | 78.16 | 73.56 | 93.10 | 97.32 | 96.01 |
| $\{M_{C, Nr}\}_j$ | 80.38 | 86.92 | 84.62 | 96.97 | 99.45 | 98.58 |
| Using selected features | | | | | | |
| $\{M_{A, Nr}\}_j$ | 83.92 | 81.63 | 83.27 | 98.92 | 99.33 | 99.03 |
| $\{M_{P, Nr}\}_j$ | 81.03 | 79.99 | 80.59 | 96.82 | 98.36 | 97.46 |
| $\{M_{P, Nr}\}_j$ | 81.03 | 79.99 | 80.59 | 96.82 | 98.36 | 97.46 |
| $\{M_{Bo, Nr}\}_j$ | 90.21 | 90.33 | 90.26 | 98.33 | 99.03 | 98.64 |
| $\{M_{BC, Nr}\}_j$ | 72.26 | 80.60 | 78.01 | 97.56 | 98.66 | 98.32 |
| $\{M_{C, Nr}\}_j$ | 87.33 | 87.96 | 87.74 | 97.98 | 99.64 | 99.05 |

It can be seen from Table 5, that after feature selection all the LR models were able to separate normal coughs from disease coughs with a very high accuracy.

LR Model between disease subgroups: Our next target is to explore the performance of the LR signatory models in classifying coughs from two different disease groups. This exploration will assist in determining how well LR models have captured the signatures of a disease. Table 6(A) present the leave-one-out validation results for this exploration when all the features were used for model training.

TABLE 6 (A)

Leave-one-out validation performance of the signatory LR models when all the features are used for model training.

| LOOV Models | Cough features only | | | Cough plus simple clinical features | | |
|---|---|---|---|---|---|---|
| $j = 1, 2, \ldots N_k$ | Sensitivity | Specificity | Accuracy | Sensitivity | Specificity | Accuracy |
| $\{M_{A,P}\}_j$ | 57.56 | 51.42 | 55.37 | 75.08 | 71.87 | 73.94 |
| $\{M_{A,Bo}\}_j$ | 46.37 | 88.93 | 60.37 | 79.39 | 90.46 | 83.03 |
| $\{M_{A,Bc}\}_j$ | 63.08 | 34.51 | 58.76 | 79.34 | 64.14 | 77.05 |
| $\{M_{A,C}\}_j$ | 73.80 | 84.30 | 75.66 | 92.41 | 86.10 | 91.29 |
| $\{M_{A,U}\}_j$ | 73.01 | 56.99 | 70.34 | 90.67 | 88.19 | 90.26 |
| $\{M_{A,R}\}_j$ | 57.07 | 61.66 | 59.92 | 71.61 | 73.11 | 72.54 |
| $\{M_{P,Bo}\}_j$ | 79.63 | 79.39 | 79.52 | 83.21 | 84.31 | 83.73 |
| $\{M_{P,Bc}\}_j$ | 66.20 | 44.11 | 60.82 | 68.95 | 46.82 | 63.56 |
| $\{M_{P,C}\}_j$ | 84.91 | 78.36 | 83.08 | 75.97 | 85.99 | 78.78 |
| $\{M_{P,U}\}_j$ | 68.69 | 58.07 | 65.87 | 72.96 | 64.46 | 70.70 |
| $\{M_{P,R}\}_j$ | 54.64 | 63.98 | 62.02 | 67.47 | 74.38 | 72.93 |
| $\{M_{Bo,Bc}\}_j$ | 67.83 | 74.97 | 69.73 | 9.20 | 97.43 | 32.72 |
| $\{M_{Bo,C}\}_j$ | 67.39 | 90.58 | 74.46 | 8.31 | 98.54 | 35.83 |
| $\{M_{Bo,U}\}_j$ | 83.96 | 78.31 | 82.33 | 57.21 | 94.46 | 68.01 |
| $\{M_{Bo,R}\}_j$ | 14.07 | 99.38 | 83.52 | 86.77 | 89.25 | 88.79 |
| $\{M_{Bc,C}\}_j$ | 68.06 | 77.69 | 73.33 | 46.96 | 95.63 | 73.57 |
| $\{M_{Bc,U}\}_j$ | 39.38 | 61.57 | 51.12 | 49.66 | 62.41 | 56.41 |
| $\{M_{BC,R}\}_j$ | 36.67 | 68.10 | 65.97 | 40.19 | 71.90 | 69.76 |
| $\{M_{C,U}\}_j$ | 37.00 | 88.43 | 61.79 | 82.06 | 86.39 | 84.15 |
| $\{M_{C,R}\}_j$ | 75.45 | 83.76 | 83.08 | 81.39 | 91.93 | 91.07 |
| $\{M_{Hw,Lw}\}_j$ | 69.43 | 67.46 | 68.44 | 69.36 | 69.78 | 69.57 | and table 6(B)—over page—presents the results after feature selection.

TABLE 6 (B)

Leave-one-out validation performance of the signatory LR models when selected features are used for model training.

| LOOV Models | Cough features only | | | Cough plus simple clinical features | | |
|---|---|---|---|---|---|---|
| $j = 1, 2, \ldots N_k$ | Sensitivity | Specificity | Accuracy | Sensitivity | Specificity | Accuracy |
| $\{M_{A,P}\}_j$ | 61.10 | 59.49 | 60.52 | 77.68 | 77.15 | 77.49 |
| $\{M_{A,Bo}\}_j$ | 82.77 | 81.55 | 82.37 | 90.77 | 90.56 | 90.70 |
| $\{M_{A,Bc}\}_j$ | 64.57 | 49.93 | 62.36 | 81.75 | 72.67 | 80.38 |
| $\{M_{A,C}\}_j$ | 85.47 | 81.28 | 84.73 | 94.00 | 89.24 | 93.16 |
| $\{M_{A,U}\}_j$ | 74.26 | 65.90 | 72.87 | 92.50 | 87.47 | 91.66 |
| $\{M_{A,R}\}_j$ | 61.24 | 62.74 | 62.17 | 75.51 | 76.43 | 76.08 |
| $\{M_{P,Bo}\}_j$ | 81.73 | 81.21 | 81.48 | 86.66 | 86.18 | 86.43 |
| $\{M_{P,Bc}\}_j$ | 68.08 | 60.89 | 66.33 | 71.35 | 61.30 | 68.90 |
| $\{M_{P,C}\}_j$ | 85.91 | 82.40 | 84.93 | 91.76 | 89.69 | 91.18 |
| $\{M_{P,U}\}_j$ | 71.96 | 63.61 | 69.74 | 76.28 | 71.81 | 75.09 |
| $\{M_{P,R}\}_j$ | 60.49 | 64.65 | 63.78 | 70.82 | 75.74 | 74.71 |
| $\{M_{Bo,Bc}\}_j$ | 86.82 | 81.33 | 85.35 | 93.06 | 89.58 | 92.14 |
| $\{M_{Bo,C}\}_j$ | 85.74 | 84.98 | 85.50 | 87.90 | 81.95 | 86.09 |
| $\{M_{Bo,U}\}_j$ | 85.74 | 83.25 | 85.02 | 90.75 | 92.05 | 91.13 |
| $\{M_{Bo,R}\}_j$ | 80.87 | 81.80 | 81.63 | 89.57 | 90.32 | 90.18 |
| $\{M_{Bc,C}\}_j$ | 76.59 | 82.06 | 79.58 | 46.96 | 95.63 | 73.57 |
| $\{M_{Bc,U}\}_j$ | 58.86 | 62.89 | 60.99 | 62.25 | 67.59 | 65.07 |
| $\{M_{BC,R}\}_j$ | 55.89 | 67.08 | 66.32 | 62.65 | 71.94 | 71.31 |
| $\{M_{C,U}\}_j$ | 80.27 | 83.37 | 81.77 | 89.46 | 90.84 | 90.13 |
| $\{M_{C,R}\}_j$ | 78.59 | 84.42 | 83.94 | 85.99 | 92.10 | 91.61 |
| $\{M_{Hw,Lw}\}_j$ | 72.99 | 72.98 | 72.99 | 73.69 | 73.73 | 73.71 |

According to Table 6(B), after the feature selection, most of the LR signatory models achieved moderate to high accuracy (70-90%) in separating coughs from two classes. The highest accuracy is achieved in identifying Croup or Bronchiolitis coughs from any other disease or group of diseases. The least accurate LR signatory models were Pneumonia vs Bronchitis and Bronchitis Vs pURTI (accuracy ~65%).

C. Performance of the Soft-Max Models on the Training-Validation Dataset

TABLE 7 (A)

Leave-one-out validation performance of the signatory LR models when all the features are used for model training.

| LOOV Models | Cough features only | | | Cough plus simple clinical features | | |
|---|---|---|---|---|---|---|
| $j = 1, 2, \ldots N_k$ | Sensitivity | Specificity | Accuracy | Sensitivity | Specificity | Accuracy |
| $\{M_{A,P}\}_j$ | 57.56 | 51.42 | 55.37 | 75.08 | 71.87 | 73.94 |
| $\{M_{A,Bo}\}_j$ | 46.37 | 88.93 | 60.37 | 79.39 | 90.46 | 83.03 |
| $\{M_{A,Bc}\}_j$ | 63.08 | 34.51 | 58.76 | 79.34 | 64.14 | 77.05 |
| $\{M_{A,C}\}_j$ | 73.80 | 84.30 | 75.66 | 92.41 | 86.10 | 91.29 |
| $\{M_{A,U}\}_j$ | 73.01 | 56.99 | 70.34 | 90.67 | 88.19 | 90.26 |
| $\{M_{A,R}\}_j$ | 57.07 | 61.66 | 59.92 | 71.61 | 73.11 | 72.54 |
| $\{M_{P,Bo}\}_j$ | 79.63 | 79.39 | 79.52 | 83.21 | 84.31 | 83.73 |
| $\{M_{P,Bc}\}_j$ | 66.20 | 44.11 | 60.82 | 68.95 | 46.82 | 63.56 |
| $\{M_{P,C}\}_j$ | 84.91 | 78.36 | 83.08 | 75.97 | 85.99 | 78.78 |
| $\{M_{P,U}\}_j$ | 68.69 | 58.07 | 65.87 | 72.96 | 64.46 | 70.70 |
| $\{M_{P,R}\}_j$ | 54.64 | 63.98 | 62.02 | 67.47 | 74.38 | 72.93 |
| $\{M_{Bo,Bc}\}_j$ | 67.83 | 74.97 | 69.73 | 9.20 | 97.43 | 32.72 |
| $\{M_{Bo,C}\}_j$ | 67.39 | 90.58 | 74.46 | 8.31 | 98.54 | 35.83 |
| $\{M_{Bo,U}\}_j$ | 83.96 | 78.31 | 82.33 | 57.21 | 94.46 | 68.01 |
| $\{M_{Bo,R}\}_j$ | 14.07 | 99.38 | 83.52 | 86.77 | 89.25 | 88.79 |
| $\{M_{Bc,C}\}_j$ | 68.06 | 77.69 | 73.33 | 46.96 | 95.63 | 73.57 |
| $\{M_{Bc,U}\}_j$ | 39.38 | 61.57 | 51.12 | 49.66 | 62.41 | 56.41 |
| $\{M_{BC,R}\}_j$ | 36.67 | 68.10 | 65.97 | 40.19 | 71.90 | 69.76 |
| $\{M_{C,U}\}_j$ | 37.00 | 88.43 | 61.79 | 82.06 | 86.39 | 84.15 |
| $\{M_{C,R}\}_j$ | 75.45 | 83.76 | 83.08 | 81.39 | 91.93 | 91.07 |
| $\{M_{Hw,Lw}\}_j$ | 69.43 | 67.46 | 68.44 | 69.36 | 69.78 | 69.57 |

The results from section 3 (B) indicated that LR-signatory models were fairly successful in capturing the disease specific signatures. Using these signatures in section 2(C) step 3, we trained a soft-max neural network model to separate a target disease coughs from other diseases. Then using Cough Index and applying an optimal threshold we achieved our ultimate target of classifying diseases at the patient level.

Table 7(B) shows the leave-one-out validation results of separating one disease from rest using Soft-max ANN models. According to these results all the models except Pneumonia, are able to predict target disease with very high sensitivity and specificity. The best validation results are obtained for croup model with 100% sensitivity and 96% specificity (using cough plus simple clinical sign model) and 95% sensitivity and 92% specificity (cough only model). Second best results are for Bronchiolitis model followed by primary URTI, Asthma and LRTD models. For all the models trained with cough plus simple clinical features clearly outperformed model trained using cough only features.

TABLE 7(B)

Leave-one-out validation results for classifying patients using soft-max ANN models

| Soft-max ANN models | Cough features only | | | Cough plus simple clinical features | | |
|---|---|---|---|---|---|---|
| | Sensitivity | Specificity | Accuracy | Sensitivity | Specificity | Accuracy |
| $S_{Bo}$ | 92.08 | 89.42 | 89.87 | 95.05 | 93.81 | 94.02 |
| $S_C$ | 94.74 | 92.29 | 92.52 | 100.00 | 95.78 | 96.18 |
| $S_A$ | 81.62 | 69.84 | 74.42 | 91.88 | 87.77 | 89.37 |
| $S_P$ | 90.98 | 44.79 | 54.15 | 90.16 | 61.67 | 67.44 |
| $S_{LRTD}$ | 85.77 | 81.82 | 85.05 | 90.24 | 88.18 | 89.87 |
| $S_U$ | 86.79 | 83.06 | 83.39 | 90.56 | 89.62 | 89.70 |

The leave-one-out cross-validation process will results in N number of soft-max models. Where N is the number of patient in TrV dataset. From the N models, we selected one of the best model again following the k-mean clustering algorithm. Table 8 shows the performance of the selected ANN models.

TABLE 8

Performance of the picked soft-max ANN models on the Training-Validation dataset

| Soft-max ANN models | Cough features only | | | Cough plus simple clinical features | | |
|---|---|---|---|---|---|---|
| | Sensitivity | Specificity | Accuracy | Sensitivity | Specificity | Accuracy |
| $S^s_{Bo}$ | 94.06 | 89.82 | 90.53 | 95.05 | 93.81 | 94.02 |
| $S^s_C$ | 96.49 | 92.29 | 92.69 | 100 | 96.51 | 96.84 |
| $S^s_A$ | 80.34 | 70.65 | 74.42 | 91.88 | 88.59 | 89.87 |
| $S^s_P$ | 89.34 | 49.17 | 57.31 | 91.80 | 92.92 | 68.77 |
| $S^s_{LRTD}$ | 85.57 | 81.82 | 84.88 | 90.24 | 88.18 | 89.87 |
| $S^s_U$ | 88.68 | 83.97 | 84.38 | 92.45 | 90.35 | 90.53 |

From table 7(B) and table 8 it could be observed that Croup, Bronchiolitis, URTI and Asthma models, all are very sensitive and specific at the same time. On the other hand Pneumonia model have a moderate specificity with a high sensitivity. Therefore we hypothesize that it could be possible to use other disease models within the Pneumonia model as post-screeners to screen out false positive cases and improve its specificity. To test this hypothesis the Inventors sequentially applied Asthma, primary URTI, Croup and Bronchiolitis models as post-screeners in Pneumonia model. To avoid true positive cases of Pneumonia screened out as other diseases we used a threshold applied to the Cough Index of the screening model. This threshold indicated how confidently a screening model is indicating subject is not-Pneumonia. Screening threshold were optimized using Training-validation dataset.

Table 9 (above) shows the results of applying different disease post-screeners sequentially to the Pneumonia model. It can be seen that with a minor loss in sensitivity, a gain in specificity of ANN pneumonia model is achieved. The loss in sensitivity was −9% for cough only model and −4% for cough plus simple clinical feature model. The gain in specificity was 18% for cough only model and 16% for cough plus simple clinical feature model. While not essential, post-screeners and pre-screeners may be used in embodiments of the invention.

Encouraged by the positive effect of post-screeners on Pneumonia model, we explored their application on other disease models. Our analysis indicated that Bronchiolitis and LRTD models specificity performance can be improved by 1 to 3% by using Croup screener. No improvement in performance is seen in Asthma and primary URTI models. As croup model performance is already very high, no screeners are tried. Table 10 shows the results of this investigation.

TABLE 9

Results of soft-max Pneumonia model after applying post-screeners.

| Post-screeners on $S^s_P$ | Cough features only | | | Cough plus simple clinical features | | |
|---|---|---|---|---|---|---|
| | Sensitivity | Specificity | Accuracy | Sensitivity | Specificity | Accuracy |
| Without post-screener | 89.34 | 49.17 | 57.03 | 91.80 | 62.92 | 68.77 |
| After Asthma post-screener | 81.15 | 60 | 64.29 | 90.98 | 65.83 | 70.93 |
| After primary URTI post-screener | 81.15 | 61.04 | 65.11 | 90.16 | 70.63 | 74.58 |
| After Croup post-screener | 81.15 | 62.92 | 66.61 | 90.16 | 74.38 | 77.58 |
| After Bronchiolitis post-screener | 80.33 | 66.67 | 69.43 | 88.53 | 79.38 | 81.22 |

TABLE 10

Results of applying post-screeners to other disease models.

| | Cough features only | | | Cough plus simple clinical features | | |
|---|---|---|---|---|---|---|
| | Sensitivity | Specificity | Accuracy | Sensitivity | Specificity | Accuracy |
| Post-screeners on $S^s_{Bo}$ | | | | | | |
| Without post-screener | 94.06 | 89.82 | 90.53 | 95.05 | 93.81 | 94.02 |
| After Croup post-screener | 94.06 | 90.62 | 91.20 | 95.05 | 94.01 | 94.19 |
| Post-screeners on $S^s_{LRTD}$ | | | | | | |
| Without post-screener | 85.57 | 81.82 | 84.88 | 90.24 | 88.18 | 89.87 |
| After Croup post-screener | 85.57 | 84.55 | 85.38 | 90.04 | 91.82 | 90.37 |
| Post-screeners on $S^s_A$ | | | | | | |
| Without post-screener | 80.34 | 70.65 | 74.42 | 91.88 | 88.59 | 89.87 |
| After Croup post-screener | 80.34 | 70.65 | 74.42 | 91.45 | 88.85 | 89.86 |
| After Bronchiolitis post-screener | 80.34 | 70.92 | 74.58 | 91.45 | 88.85 | 89.86 |
| Post-screeners on $S^s_U$ | | | | | | |
| Without post-screener | 88.68 | 83.97 | 84.38 | 92.45 | 90.35 | 90.53 |
| After Croup post-screener | 88.68 | 83.97 | 84.38 | 92.45 | 90.71 | 90.86 |
| After Bronchiolitis post-screener | 86.79 | 84.15 | 84.38 | 90.56 | 90.89 | 90.86 |

D. Performance of the Soft-Max Models on the Prospective Testing Dataset

Figure 3:
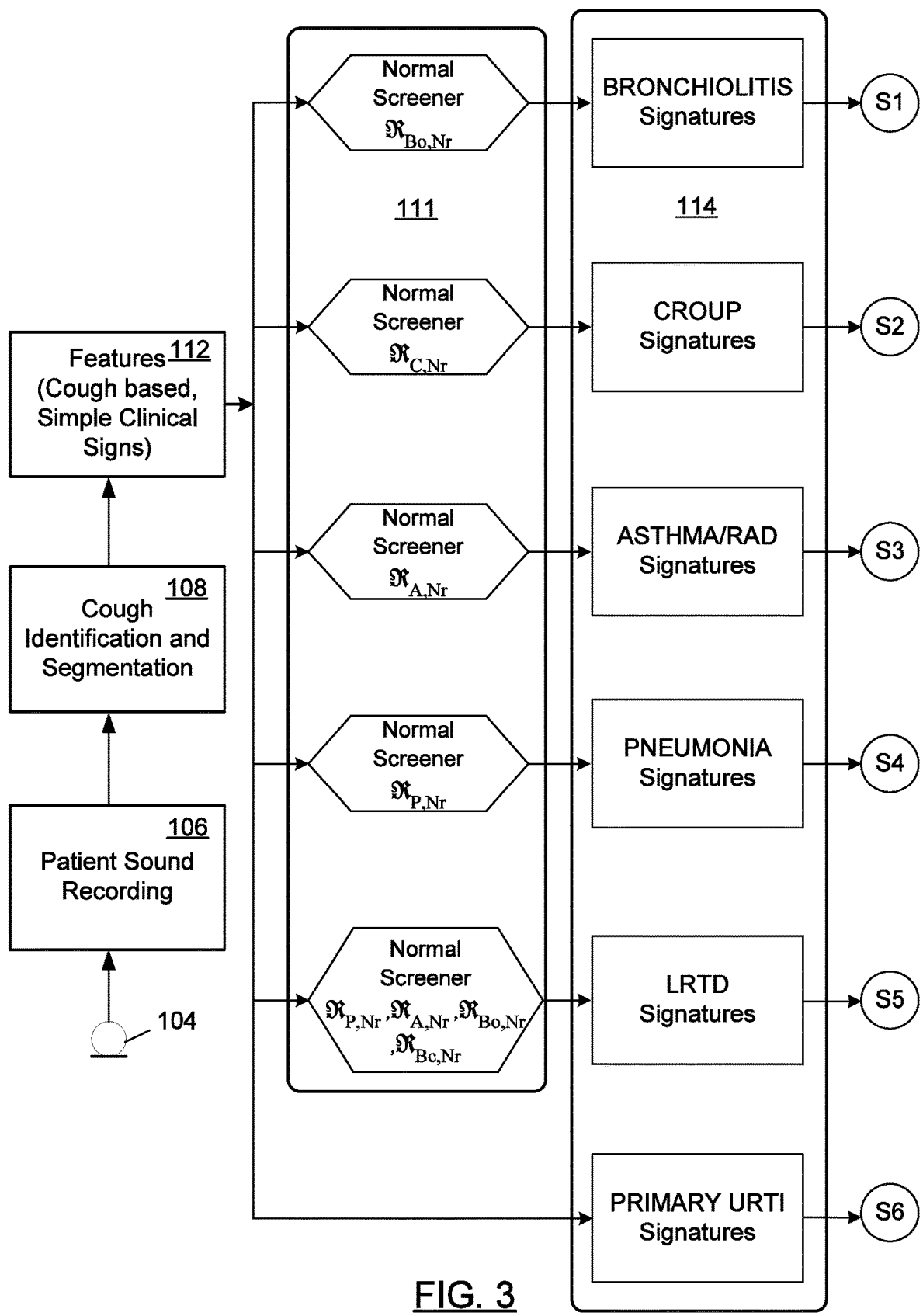
FIG. 3 Is a first portion of a flowchart of a diagnostic method according to a further embodiment of the present invention that includes pre-screening and post-screening processing blocks.

FIG. 3 shows a flowchart 300 of the diagnostic algorithms after all the training is over with all the parameters fixed and selected models are ready for prospective testing. These models were tested on the prospective dataset which is completely independent of the training-validation dataset. All the models except for pneumonia achieved high accuracy in predicting the target disease. Among all the models Croup and Bronchiolitis were found to be the best achieving sensitivities and specificities in the range 86%-100% across all the prospective study lists and for both cough only and cough plus simple clinical feature models. The performance of the Asthma/RAD model was moderate with cough only feature, however it improved significantly (Sensitivity ~93% and Specificity ~90%) with the addition of simple clinical features to cough features. See Appendix E for details on the Pre-Screener and the Post-Screener Blocks.

1. Appendix A
   1. Clinical Pneumonia
      US Clinical Pneumonia Case Definition—as used in labelling the data sets from JHC & PMH
   2. WHO Radiological Primary End Point Pneumonia (PEP)
      US WHO Radiological Pneumonia Case Definition—as used in labelling the X-ray data sets from JHC & PMH
   3. Croup
      US Clinical Croup Case Definition—as used in labelling the data sets from JHC & PMH
   4. Bronchiolitis
      US Bronchiolitis Case Definition—as used in labelling the data sets from JHC & PMH
   5. Asthma (A)/Reactive Airway Disease (RAD)—A/RAD
      US A/RAD Case Definition—as used in labelling the data sets from JHC & PMH
   6. Bronchitis
      US bronchitis Case Definition—as used in labelling the data sets from JHC & PMH
   7. Upper Respiratory Tract Infections
      US URTI Case Definition—as used in labelling the data sets from JHC & PMH
   8. Lower Respiratory Tract Disease (LRTD)
      US LRTD Case Definition—as used in labelling the data sets from JHC & PMH
2. Appendix B
   Computing Features from Coughs
   Cough Features
   Our method requires the computation of a number of mathematical features from cough sounds. This Section describes the features we computed from each sub-segment $x_i$, i=1, 2, 3 of a recorded cough sound x.
   i) Bispectrum Frequency Cepstral Coefficients (BFCC, total 24 features; 8 from each part of cough segment)—The $3^{rd}$ order spectrum of a signal is known as the bispectrum[3]. Unlike the power spectrum (the $2^{nd}$ order spectrum based on the autocorrelation), the bispectrum preserves Fourier phase information. The bispectrum $B_{xi}(\omega_1,\omega_2)$ of the segment $x_i$ can be estimated from (6) as, $$B_{xi}(\omega_1, \omega_2) = \sum_{\tau_1=-\infty}^{\tau_1=+\infty} \sum_{\tau_2=-\infty}^{\tau_2=+\infty} W(\tau_1, \tau_2) \cdot C_{xi}(\tau_1, \tau_2) e^{-j(\tau_1\omega_1+\tau_2\omega_2)}, \quad (6)$$

where $W(\tau_1,\tau_2)$ is a bispectrum window function such as the minimum bispectrum-bias supremum window used in this paper, $C_{xi}(\tau_1,\tau_2)$ is the third order cumulants of $x_i$ estimated with (2), and, $\omega_1$, $\omega_2$ denotes digital frequencies.

$$C_{xi}(\tau_1, \tau_2) = \frac{1}{L}\sum_{k=0}^{L-1} x_i[k]x_i[k+\tau_1]x_i[k+\tau_2], |\tau_1| \le Q, |\tau_2| \le Q \quad (7)$$

In (7), Q is the length of the $3^{rd}$ order correlation lags considered and $x_i$ is a zero-mean signal.

The bispectrum is a 2D signal. However, it can be proven that for linear signals, any 1D oblique slice of the bispectrum other than the slices parallel to the axes: $\omega_1=0$, $\omega_2=0$ and $\omega_1+\omega_2=0$ carries sufficient information to characterise the entire 2D bispectrum within a phase factor. In this work, we capture the information available in the bispectrum via the diagonal slice $P(\omega)$ defined by $\omega_1+\omega_2=\omega$, i.e. $P(\omega)=B_{xi}(\omega, \omega)$.

Then applying a filter operator to the diagonal slice $P(\omega)$ we computed the Bispectrum Frequency Cepstral Coefficients using (8).

$$BFCC = \sum_{\omega=\omega_l}^{\omega_h} P(\omega) \cdot \zeta(\omega) \cdot \vartheta \quad (8)$$

In (8) $\zeta$ represent a filter operator with $\omega_l$ and $\omega_h$ as its lower and higher cut-off frequencies and $\theta$ is a gain constant of the filter. In (8) $\zeta$ could be a triangular filter, rectangular filter, trapezoidal filter or more complex shapes one. For the work of this paper we used a rectangular filter with $\theta=1$ and computed 8 BFCC coefficients using following $\omega_l$ and $\omega_h$ values as shown in Table 11:

TABLE 11

The filter lower and high cut-off values used in eq. (8) to compute BFCC coefficients.

| | BFCC1 | BFCC2 | BFCC3 | BFCC4 | BFCC5 | BFCC6 | BFCC7 | BFCC8 |
|---|---|---|---|---|---|---|---|---|
| $\omega_l$ (Hz) | 1 | 86 | 259 | 603 | 1292 | 2670 | 5426 | 10939 |
| $\omega_h$ (Hz) | 172 | 345 | 689 | 1378 | 2756 | 5512 | 11025 | 22050 | ii) Non-Gaussianity Score (NGS, total 3 features 1 from each part of cough segment)—NGS score is a numerical measure of non-Gaussianity of a given segment of data $x_i$. The normal probability plot can be utilized to obtain a visual measure of the Gaussianity of a set of data, and the NGS score is a way of quantifying the non-Gaussianity based on regression analysis. We used (9) to estimate the NGS score, where p and q represents the normal probability plots of the reference normal data and the analysed data ($x_i$). The symbol N is the number of data points used in the probability plot.

$$NGS = 1 - \left(\frac{\sum_{j=1}^{N}(q[j]-p)^2}{\sum_{j=1}^{N}(q[j]-\bar{q})^2}\right) \quad (9)$$

iii) Formant frequencies (total 12 features 4 from each part of cough segment)—In speech analysis, formants frequencies (FF) are referred to as the resonances of the vocal tract. In cough analysis, it is reasonable to expect that the resonances of the overall airway that contribute to the generation of a cough sound will be represented in the formant structure. One classic example for this is wheeze. Existence of mucous can also change acoustic properties of airways. We included the first four formants (F1, F2, F3, F4) in our candidate feature set. We computed F1-F4 by peak picking the Linear Predictive Coding (LPC) spectrum of cough segments $x_i$. For this work we used a $14^{th}$ order LPC model with the parameters determined via the Levinson-Durbin recursive procedure.

iv) Log Energy (Log E, total 3 features 1 from each part of cough segment)—The log energy for every sub-segment $x_i$ was computed using (10):

$$LogE = 10\log_{10}\left(\varepsilon + \frac{1}{N}\sum_{k=1}^{K}(x_i[k]^2)\right) \quad (10)$$

In (4) $\varepsilon$ is an arbitrarily small positive constant added to prevent any inadvertent computation of the logarithm of 0.

v) Zero crossing (Zcr, total 3 features 1 from each part of cough segment)—The number of zero crossings was counted for each sub-segment $x_i$.

vi) Kurtosis (Kurt, total 3 features 1 from each part of cough segment)—The kurtosis is a measure of how peaky the probability density distribution of $x_i$ is. It is the fourth central moment of $x_i$ and can be computed using (11), where $\mu$ and $\sigma$ respectively denote the mean and the standard deviation of $x_i$.

$$Kurt = \frac{E\{(x_i[k]-\mu)^4\}}{\sigma^4} \quad (11)$$

vii) Mel-Frequency Cepstral coefficients (MFCC, total 93 features 31 from each part of cough segment)—MFCCs have been widely used in speech recognition systems. MFCC provides some resilience to the non-linguistic sources of variance in speech signals. They also provide orthogonal features making facilitating the training of the classifier. The computation of MFCC involves the estimation of short-term power spectra, mapping to Mel frequency scale and then computing the cepstral coefficients. In our work, we included 31 MFCC coefficients in our feature set.

viii) Shannon Entrophy (ShE, total 3 features 1 from each part of cough segment): Cough sound is a complex signal which represents contributions from various sub-structures of the respiratory tract. Some of these components display pseudo-periodic structures, while others have a random stochastic character. In this work we computed the Shannon entropy to capture these features. The Shannon entropy (ShE) of every sub-segment $x_i$ was computed using (12)

$$ShE = -\sum_{k=1}^{K-1} (\hat{x}_i[k]^2) \ln(\hat{x}_i[k]^2) \quad (12)$$

ix) Wavelet Features (WvL, total 13 features from each cough): Our previous research have shown the usefulness of wavelet features from cough sounds in pneumonia diagnosis [refer ieee trans paper]. For this work we computed 13 wavelet features from each cough segments. For details please see [2].

3. APPENDIX C

1. Wheeze Signature Generator

Wheezing in children is a common symptom of many respiratory diseases. Wheezing is defined as a high-pitched whistling sound produced during the breathing. Wheeze is most commonly associated with Asthma, however it is also present in other respiratory diseases such as bronchiolitis, bronchitis, pneumonia, cystic fibrosis and aspiration of foreign material etc. It is often used in differential diagnosis and separating Lower respiratory tract diseases from upper respiratory tract infections. More details are available in Appendix A: Case Definitions.

The existence or otherwise of wheeze is a key decision node in the clinical decision tree as practiced by the clinical community. However, it is not always a straightforward task to clinically detect it. Wheeze is a temperamental phenomenon, and a secondary effect of an underlying change in physiology/pathology. The ability of a physician to detect wheeze at a particular time of examination depends on many factors including the wheeze being existent at the time, and the clinician placing the stethoscope on the right spot over lungs, wheeze sounds being generated at a strong-enough intensity to survive energy losses while propagating from the lungs to the surface of the torso and the clinician can perceive the sounds and have the skills to detect it. The underlying physiological reason of interest is the narrowing of airway due to various reasons and wheeze is a surrogate measure of that phenomenon. In some situations the wheeze may not arise even if it is severe disease because of limitations in airflow due to the severity of the disease (e.g. "silent chest" in severe Asthma/RAD).

In order to capture the severity of wheeze, clinicians have defined many different versions of Wheeze Severity Scores (WSS). The version our clinical collaborators use three different subscores to compute the WSS. These are: existence of wheeze and during which respiratory phase it occurs, breathing rate, accessory muscle use. We have developed one signature to capture the WSS using cough alone or augmented with simple signs a parent can observe. Our WSS model was trained on a target of separating high WSS (5-9) from low WSS scores (0,1) using a continuous signature scale (the LRM output) varying between between 0-1.

2. Lung Function Signature Generator

Lung function laboratory techniques, especially spirometry, are used in the definitive diagnosis of some respiratory diseases such as asthma and chronic obstructive pulmonary disease (COPD) when available. Spirometry provide numerical measurements such as the FEV1 and FVC. Using coughs collected at the time of spirometry, we built cough-based signature models such as: high FEV1 vs low FEV1, high FEV1/FVC vs low FEV1/FVC. Once trained, they are then used on all patients as a signature generator providing an output between (0,1).

4. APPENDIX D

Clinical Sign-Based Signatures and Diagnostic Models

Clinicians rely heavily on clinical signs (either they observed or parents reported) in diagnosing some respiratory diseases. Previously we had investigated and built models to identify the best clinical features to diagnose pneumonia (Indonesian study) based on clinical signs only. We also investigated what happens when we add a small number of coughs to the clinical sign models.

We have built clinical signs-only models (using signs reportable by parents) to diagnose the respiratory diseases following the architecture shown in Figure B. In a particular embodiment, signs such as fever, wheeze, runny nose, and age, gender are used to build signatures based on an LRM modelling. The LRM model transforms the categorical signs to a continuous output at the Signature Generator level, which are then classified at the level of the Classifier Block. In other embodiments other classifier schemes such as ANNs could be used for the same purpose. We also can add coughs to the clinical signs model to improve the performance as we did in the clinical signs patent filed on the Indonesian study. Furthermore, we can use the clinical-signs signatures to improve the classification using a deep learning approach.

The process of designing Neural Deep Learning Architecture is divided into two stages which are now discussed:

STAGE ONE—Layer by layer training—In the first stage we individually trained three types of neural networks to do a specific task.

Figure 5:
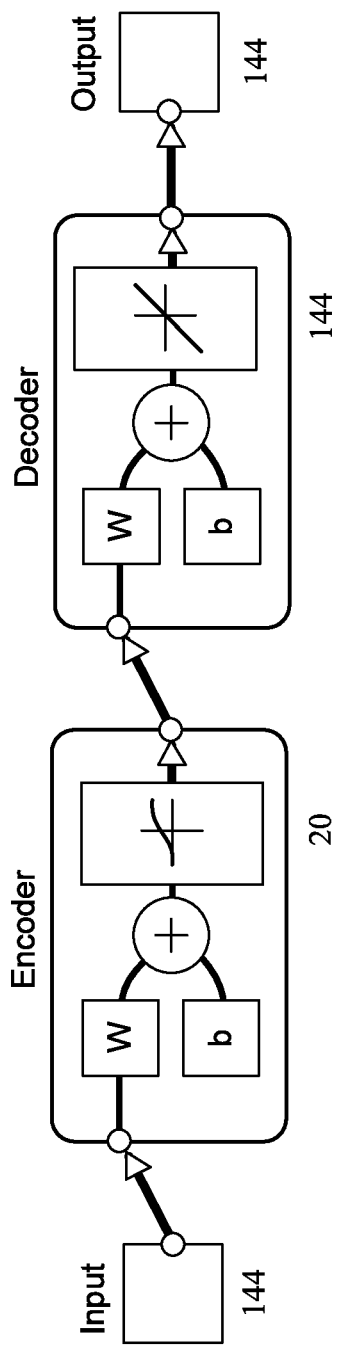
FIG. 5 Is a block diagram of an Auto-Encoder Neural Network trained for feature mapping.

Stage 1—Neural Net Type 1. Feature Encoding Neural Net (FeNN): Here we implement the concept of an Auto-Encoder. An auto-encoder is a feedforward neural network trained to reproduce its input at the output [1]. The hidden layers in an auto-encoder symbolizes a code which can be used to represent the input data. After the training, Encoder stage output is used in the next step. FIG. 5 shows an example of an auto-encoder that is trained for feature mapping. It has an input size of 144 representing the size of the input feature vector, the hidden layer (Encoder) size is 10 and the output layer (Decoder) size is 144, being the same size as the input layer.

Figure 6:
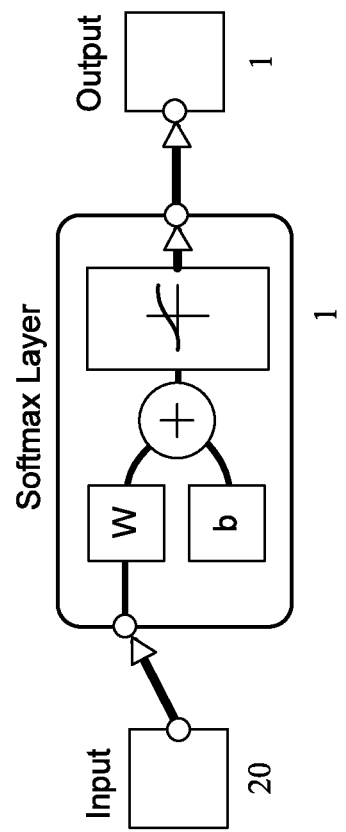
FIG. 6 Is a block diagram of a signature layer neural net that is trained to generate disease specific signatures.

Stage 1—Neural Net Type 2. Signature Neural Net (SgNN): Output from the Encoder is used to train a feedforward neural network to generate signatures as described in section "Signature Generator Block". This signatory ANN had no hidden layer and soft-max neuron in the output layer. The advantage of using soft-max neuron is that, the output will be probability function varying between 0 and 1 similar to the LR model, however now input to out mapping is non-linear. FIG. 6 shows an example of a Signature neural net. The input to this network is from the Encoder. This neural network is trained to generate disease specific signatures. In all 26 Signature Neural Nets were trained for all the signature models listed in Table 1. Table 14 presents Leave-one-out validation results in classifying normal coughs from disease coughs using signatory Neural Net models. Table 15 sets out leave-one-out validation performance of the signatory Neural Net models.

Stage 1—Neural Net Type 3. Classification Neural Net (CaNN): The output of the Signature Neural Nets were then used to train a final Classification Softmax Neural Net. This neural network is similar to those described with reference to Classifier Block 118.

In a preferred embodiment, the Inventors trained a single soft-max ANN model to identify all the target disease subgroups: Bronchiolitis, Croup, Asthma/RAD, Pneumonia and Lower respiratory tract diseases. The signatory neural nets used to train CaNN were $\{\mathfrak{R}_{Hw,Lw}, \mathfrak{R}_{A,R}, \mathfrak{R}_{A,C}, \mathfrak{R}_{A,P}, \mathfrak{R}_{A,Bo}, \mathfrak{R}_{A,Bc}, \mathfrak{R}_{A,U}, \mathfrak{R}_{A,Nr}, \mathfrak{R}_{P,Nr}, \mathfrak{R}_{Bo,Nr}, \mathfrak{R}_{BC,Nr}, \mathfrak{R}_{C,Nr}, \mathfrak{R}_{U,Nr}\}$. At the output layer dimension of the k was set to 7 neurons with each neuron corresponding to one disease subgroups, Bronchiolitis, Asthma/RAD, Pneumonia, Bronchitis, pURTI, Croup and Normal.

Figure 7:
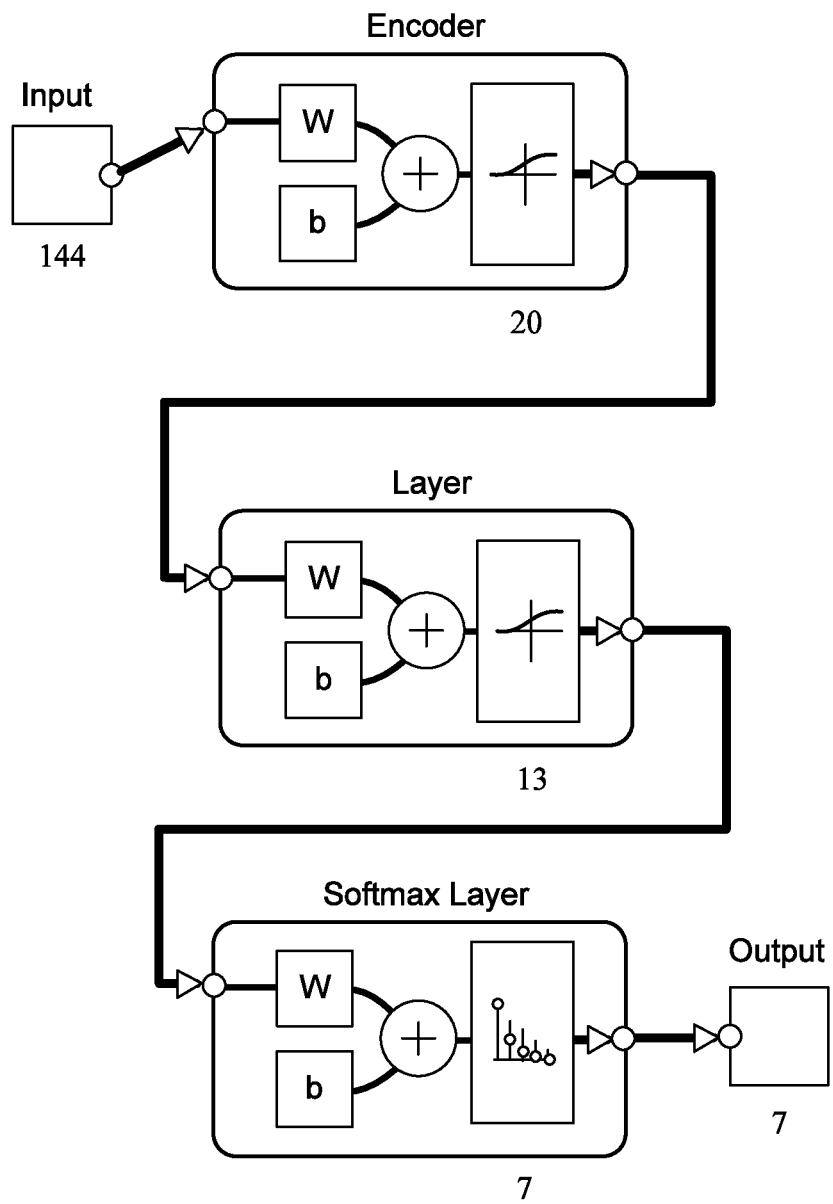
FIG. 7 Is a block diagram of a Deep Neural Network according to an embodiment of the present invention.

STAGE TWO—Fine tuning stage in this stage the the individually trained neural networks from Stage 1, were connected together to create a stacked Deep Neural Network (DNN) illustrated in FIG. 7. FIG. 7 shows the DNN in which the 1st layer represents a Feature encoding Neural Net, the $2^{nd}$ layer represents Signature Neural Nets, and 3rd output layer represents a Classification Neural Net.

The DNN is then re-trained with limited number of training epochs and using the training-validation dataset to fine-tune the DNN network parameters. Fine-tuning of DNN was done following a leave-one-out validation technique.

Table 16 presents leave-one-out validation results for classifying patients using DNN models.

5. APPENDIX E

Pre-Screeners and Post-Screeners

Figure 4:
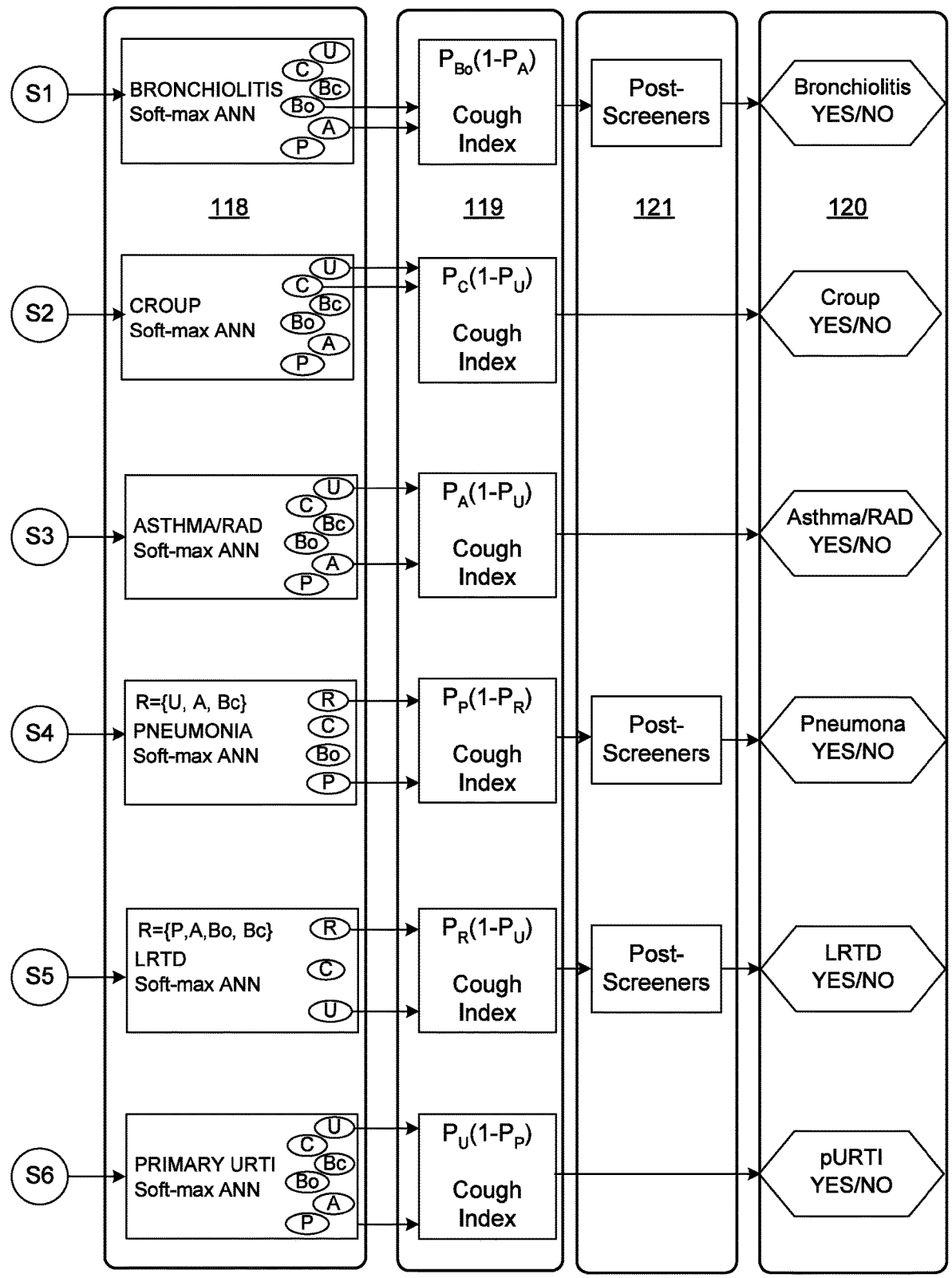
FIG. 4 Comprises the second portion of the flowchart of FIG. 3.

A further embodiment of the invention will now be described with reference to the block diagram of the diagnostic model 300 that is set out over two pages in FIGS. 4 and 5. The diagnostic model 300 comprises the Disease Signature Generation block 114 and the Classifier Block 118 of the first embodiment 100 of FIG. 1 (See FIG. 1), which may be referred to as the Primary Model. However the second embodiment of the diagnostic model 300 also includes a Pre-Screener Block 111 and a Post-Screener Block 121 to improve the diagnostic performance of the overall diagnostic method.

i) The Pre-Screener Block 111

The function of Pre-Screener block 111 is to screen out subjects who are not intended for analysis by the Primary Model.

As an example, consider the situation where the task of the Primary Model is defined as diagnosing a particular disease, say bronchiolitis, from a mix of other given diseases in a population of subjects attending a medical facility. The outcome of the overall diagnostic algorithm is: "bronchiolitis yes/no?=no" or "bronchiolitis yes/no?=yes". The pre-screener 111 in this situation can be designed to separate normal subjects from bronchiolitis cases and report the outcome as "bronchiolitis yes/no?=no" without having to send the case to the Primary Model for further analysis.

Each of the Screener Models 4a, . . . , 4n in the Screener Block 111 have decision thresholds set high to make sure persons with the actual disease being targeted in the Primary Model do not erroneously get screened out from further analysis by getting a no-disease label.

ii) The Post-Screener Block 121

The function of the Post-Screener block 121 is to improve the diagnostic performance of the Primary Model by targeting the detection of dominant false positives of the Primary Model and making a correction.

As an example, consider the situation where the task of the Primary Model is defined as diagnosing a particular disease, say bronchiolitis, from a mix of other given diseases in a population of subjects attending a medical facility. The outcome of the overall diagnostic algorithm is: "bronchiolitis yes/no?=no" or "bronchiolitis yes/no?=yes". Suppose we are aware that croup patients present as a dominant false positive group in our Primary Model. That is, in the group: "bronchiolitis yes/no?=yes", we find a sizable number of subjects with a clinical diagnosis of croup. In this scenario, our approach is to build a Post-Screener Model: {croup against bronchiolitis}, which is trained to pick croup patients from a mix of croup and bronchiolitis subjects. We will then process the "bronchiolitis yes/no?=yes" group with our {croup against bronchiolitis} model and move detected croup patients to the "bronchiolitis yes/no?=no" side of the Primary Model output.

Depending on the need and efficacy, it is possible to apply multiple Post-Screener models 6a, . . . , 6m to a given Primary Model. It is also possible that no Post-Screener is useful or necessary in a given Primary Model. When needed, Screener Models are sparingly used, with decision thresholds set high to make sure persons with the actual disease being targeted in the Primary Model do not erroneously move to the other side of the diagnostic decision.

6. APPENDIX F

Feature Reduction in Model Development

The diagnostic models discussed herein were developed using cross validation (CV) methods on the available clinical data sets. K-fold cross validation (with K=10) and leave-one-out validation (LOOV) methods were used on the available data. Both of these methods have their advantages and disadvantages. The 10-Fold CV has the tendency to lead to models with lower variance and a higher bias of estimation on new data sets (the generalization performance on previously unseen data sets); the LOOV has the tendency to lead to models with a higher variance and a lower bias on new data sets.

Due to the smaller size of the available data sets it was often preferred that the LOOV method be used over the 10-Fold in developing the diagnostic models. In order to compensate for the higher generalization variance in the models, a feature reduction process was developed, targeting the building of models are as small as possible leading to a lower risk at model over-fitting. The procedure is described in the following.

Feature optimization/reduction is a technique of selecting a subset of relevant features for building a robust classifier. Optimal feature selection requires the exhaustive search of all possible subsets of features. However, it is impractical to do so for the large number of features we use as candidate features. Therefore, an alternative approach was used based on the p value to determine significant features in the signature model designs stage using a Logistic Regression Model (LRM). In LRM design, a p-value is computed for each feature and it indicates how significant that feature is to the model. Important features have low p-values and that property of LRM was used to determine an optimal combination of features that facilitate the classification, in the model during the training phase.

The approach taken consisted of computing the mean p-values for all the features over the entire data set, and then selecting the features with mean p-values less than a threshold $P_{min}$. The detailed method is described in following steps.

1. Let $F_N = [F_1, F_2, F_3, \ldots, F_n]$ represents an initial set of all the N features.
2. Train a Logistic-regression model (LRM) using $F_N$ and following a Leave one out validation (or K-fold) process. Compute mean p value for all the features.

$$P_N = [P_{f1}, P_{f2}, P_{f3}, \ldots, P_{fn}] \quad (1)$$

In (1) $P_N$ represents a set of mean values associated with initial set of all the N features.

3. Create a new subset of feature $F'_N$ from $F_N$ by selecting those feature whose mean p value is less than $P_{ths} = P_O$.
4. Train a LRM using $F'_N$ set of features following a Leave one out validation (or K-fold) process. Compute mean p value for $F'_N$ set of feature.
5. Create a new subset of feature $F''_N$ from $F'_N$ by selecting those feature whose mean p value is less than $P_{ths}$.
6. If size of $F''_N$ is equal to $F'_N$ i.e. all the features in $F'_N$ have mean p value less than $P_{ths}$ than change the $P_{ths}$ using equation (2)

$$P_{ths} = P_{ths} - c \quad (2)$$

where, $c \ll P_{ths}$

7. Repeat Step 6. until size of $F''_N$ set is less than $F'_N$ set.
8. Reset the value of $P_{ths}$ to its original value and repeat steps 4-7, until size of $F''_N$ feature set is less than $F_{min}$.

9. For every subset of selected feature model performance (Sensitivity, Specificity and Kappa value) is computed. To pick the optimum subset of features we followed below scheme.
   a. Choose a subset of feature which have the maximum kappa value in model performance. Let this subset be $F_a$.
   b. Now identify all subset of features whose performance (in terms of sensitivity/specificity) is within q % of model performance with $F_a$ subset of features.
   c. From this pool of identified subset of features select one subset whose size is minimum, but more than Z and less than size of $F_a$. If this is not satisfied then select $F_a$ as optimum feature set.

In one particular embodiment, the following parameter values were used with the algorithm given above. Size of $F_N$ for cough only model is =157 (that is 157 input features to the LRM were started with). Size of $F_N$ for cough plus clinical sign model is 157+ and depended on number of clinical features used.

$P_{ths}$ (at Step 3)=$P_O$=0.20 c (at Step 6)=0.001

$F_{min}$ (at Step 8)=10

Z (at Step 9)=10

7. In one particular embodiment, the following parameter values with the algorithm given above were used. Results obtained with the method are given in Tables 12 and 13 below.

TABLE 12

Leave-one-out validation performance of the signatory LR models after feature optimization. Cough features only.

| LOOV Models | Train Results | | | Test Results | | |
|---|---|---|---|---|---|---|
| j = 1, 2, ... $N_k$ | Sensitivity | Specificity | Accuracy | Sensitivity | Specificity | Accuracy |
| $\{M_{A, P}\}_j$ | 63.88 | 63.89 | 63.88 | 61.03 | 60.23 | 60.74 |
| $\{M_{A, Bo}\}_j$ | 83.12 | 83.14 | 83.13 | 81.71 | 81.26 | 81.56 |
| $\{M_{A, Bc}\}_j$ | 64.21 | 64.25 | 64.22 | 63.00 | 54.40 | 61.70 |
| $\{M_{A, C}\}_j$ | 86.08 | 86.11 | 86.09 | 84.65 | 82.06 | 84.19 |
| $\{M_{A, U}\}_j$ | 74.39 | 74.42 | 74.39 | 73.03 | 68.92 | 72.34 |
| $\{M_{A, R}\}_j$ | 64.48 | 64.49 | 64.49 | 61.56 | 63.24 | 62.60 |
| $\{M_{P, Bo}\}_j$ | 82.69 | 82.71 | 82.70 | 81.12 | 81.11 | 81.11 |
| $\{M_{P, Bc}\}_j$ | 70.56 | 70.60 | 70.57 | 68.25 | 64.28 | 67.28 |
| $\{M_{P, C}\}_j$ | 86.54 | 86.58 | 86.55 | 84.82 | 82.85 | 84.27 |
| $\{M_{P, U}\}_j$ | 72.46 | 72.49 | 72.46 | 70.08 | 67.47 | 69.39 |
| $\{M_{P, R}\}_j$ | 66.09 | 66.11 | 66.10 | 61.67 | 64.88 | 64.21 |
| $\{M_{Bo, Bc}\}_j$ | 87.24 | 87.30 | 87.26 | 86.37 | 81.19 | 84.99 |
| $\{M_{Bo, C}\}_j$ | 86.81 | 86.86 | 86.83 | 85.69 | 82.96 | 84.85 |
| $\{M_{Bo, U}\}_j$ | 83.72 | 89.60 | 85.41 | 83.62 | 89.16 | 85.23 |
| $\{M_{Bo, R}\}_j$ | 81.96 | 81.97 | 81.97 | 80.18 | 81.39 | 81.16 |
| $\{M_{Bc, C}\}_j$ | 85.32 | 85.38 | 85.35 | 80.38 | 83.30 | 81.97 |
| $\{M_{Bc, U}\}_j$ | 69.28 | 69.33 | 69.30 | 64.14 | 64.82 | 64.50 |
| $\{M_{BC, R}\}_j$ | 65.74 | 65.77 | 65.77 | 59.13 | 65.47 | 65.04 |
| $\{M_{C, U}\}_j$ | 85.49 | 85.55 | 85.52 | 82.29 | 82.53 | 82.40 |
| $\{M_{C, R}\}_j$ | 83.42 | 83.44 | 83.43 | 81.05 | 82.86 | 82.71 |

TABLE 13

Leave-one-out validation performance of the signatory LR models after feature optimization. Cough plus simple clinical features

| LOOV Models | Train Results | | | Test Results | | |
|---|---|---|---|---|---|---|
| j = 1, 2, ... $N_k$ | Sensitivity | Specificity | Accuracy | Sensitivity | Specificity | Accuracy |
| $\{M_{A, P}\}_j$ | 80.66 | 81.20 | 80.86 | 78.67 | 78.02 | 78.44 |
| $\{M_{A, Bo}\}_j$ | 92.26 | 93.14 | 92.55 | 91.23 | 92.08 | 91.51 |
| $\{M_{A, Bc}\}_j$ | 82.19 | 82.31 | 82.21 | 80.79 | 74.70 | 79.87 |

TABLE 13-continued

Leave-one-out validation performance of the signatory LR models after feature optimization. Cough plus simple clinical features

| LOOV Models | Train Results | | | Test Results | | |
|---|---|---|---|---|---|---|
| $j = 1, 2, \ldots N_k$ | Sensitivity | Specificity | Accuracy | Sensitivity | Specificity | Accuracy |
| $\{M_{A,C}\}_j$ | 94.94 | 95.07 | 94.96 | 94.17 | 89.24 | 93.29 |
| $\{M_{A,U}\}_j$ | 91.92 | 91.94 | 91.92 | 91.52 | 88.31 | 90.98 |
| $\{M_{A,R}\}_j$ | 78.44 | 78.94 | 78.75 | 75.95 | 76.93 | 76.55 |
| $\{M_{P,Bo}\}_j$ | 89.00 | 90.33 | 89.63 | 87.44 | 88.64 | 88.00 |
| $\{M_{P,Bc}\}_j$ | 72.51 | 72.56 | 72.52 | 70.00 | 65.09 | 68.80 |
| $\{M_{P,C}\}_j$ | 93.20 | 93.76 | 93.36 | 91.02 | 89.57 | 90.61 |
| $\{M_{P,U}\}_j$ | 78.42 | 78.99 | 78.58 | 75.58 | 71.08 | 74.38 |
| $\{M_{P,R}\}_j$ | 76.12 | 76.88 | 76.72 | 71.61 | 75.56 | 74.73 |
| $\{M_{Bo,Bc}\}_j$ | 13.65 | 99.80 | 36.62 | 11.41 | 98.11 | 34.52 |
| $\{M_{Bo,C}\}_j$ | 15.27 | 99.67 | 41.03 | 11.41 | 98.77 | 38.05 |
| $\{M_{Bo,U}\}_j$ | 92.41 | 93.88 | 92.83 | 89.62 | 93.25 | 90.67 |
| $\{M_{Bo,R}\}_j$ | 89.93 | 90.88 | 90.71 | 88.39 | 90.22 | 89.88 |
| $\{M_{Bc,C}\}_j$ | 62.45 | 99.08 | 82.51 | 46.28 | 88.23 | 69.22 |
| $\{M_{Bc,U}\}_j$ | 75.25 | 75.31 | 75.28 | 64.82 | 67.59 | 66.28 |
| $\{M_{BC,R}\}_j$ | 72.28 | 72.58 | 72.56 | 64.01 | 72.02 | 71.48 |
| $\{M_{C,U}\}_j$ | 91.95 | 92.00 | 91.97 | 88.68 | 89.16 | 88.91 |
| $\{M_{C,R}\}_j$ | 92.04 | 92.36 | 92.33 | 87.11 | 91.97 | 91.57 |

TABLE 14

Leave-one-out validation results in classifying normal coughs from disease coughs using signatory Neural Net models. Using all the features

| LOOV Models | Cough features only | | | Cough plus simple clinical features | | |
|---|---|---|---|---|---|---|
| $j = 1, 2, \ldots N_k$ | Sensitivity | Specificity | Accuracy | Sensitivity | Specificity | Accuracy |
| $\{M_{A,Nr}\}_j$ | 75.34 | 75.30 | 75.33 | 79.39 | 79.38 | 79.39 |
| $\{M_{P,Nr}\}_j$ | 73.62 | 73.60 | 73.61 | 77.10 | 77.07 | 77.09 |
| $\{M_{Bo,Nr}\}_j$ | 82.10 | 82.06 | 82.08 | 88.54 | 88.50 | 88.52 |
| $\{M_{BC,Nr}\}_j$ | 73.61 | 73.60 | 73.60 | 75.91 | 75.85 | 75.87 |
| $\{M_{C,Nr}\}_j$ | 82.74 | 82.73 | 82.73 | 87.67 | 87.65 | 87.66 |

TABLE 15

Leave-one-out validation performance of the signatory Neural Net models.

| LOOV Models | Cough features only | | | Cough plus simple clinical features | | |
|---|---|---|---|---|---|---|
| $j = 1, 2, \ldots N_k$ | Sensitivity | Specificity | Accuracy | Sensitivity | Specificity | Accuracy |
| $\{M_{A,P}\}_j$ | 60.64 | 60.62 | 60.63 | 60.88 | 60.88 | 60.88 |
| $\{M_{A,Bo}\}_j$ | 78.16 | 78.16 | 78.16 | 78.93 | 78.90 | 78.92 |
| $\{M_{A,Bc}\}_j$ | 61.32 | 61.30 | 61.31 | 59.97 | 59.95 | 59.96 |
| $\{M_{A,C}\}_j$ | 78.26 | 78.25 | 78.26 | 79.61 | 79.60 | 79.61 |
| $\{M_{A,U}\}_j$ | 67.73 | 67.71 | 67.72 | 68.11 | 68.07 | 68.11 |
| $\{M_{A,R}\}_j$ | 61.10 | 61.09 | 61.09 | 60.83 | 60.82 | 60.83 |
| $\{M_{P,Bo}\}_j$ | 77.93 | 77.91 | 77.92 | 78.94 | 78.90 | 78.92 |
| $\{M_{P,Bc}\}_j$ | 65.37 | 65.36 | 65.37 | 65.24 | 65.22 | 65.24 |
| $\{M_{P,C}\}_j$ | 80.42 | 80.38 | 80.41 | 82.64 | 82.62 | 82.64 |
| $\{M_{P,U}\}_j$ | 65.20 | 65.18 | 65.19 | 64.33 | 64.22 | 64.30 |
| $\{M_{P,R}\}_j$ | 61.62 | 61.62 | 61.62 | 62.23 | 62.22 | 62.23 |
| $\{M_{Bo,Bc}\}_j$ | 83.67 | 83.63 | 83.66 | 85.49 | 85.39 | 85.46 |
| $\{M_{Bo,C}\}_j$ | 81.85 | 81.84 | 81.85 | 83.13 | 83.07 | 83.11 |
| $\{M_{Bo,U}\}_j$ | 81.85 | 81.81 | 81.84 | 83.37 | 83.37 | 83.37 |
| $\{M_{Bo,R}\}_j$ | 77.08 | 77.08 | 77.08 | 77.96 | 77.96 | 77.96 |
| $\{M_{Bc,C}\}_j$ | 78.76 | 78.70 | 78.72 | 81.06 | 81.05 | 81.05 |
| $\{M_{Bc,U}\}_j$ | 64.82 | 64.70 | 64.75 | 64.68 | 64.58 | 64.63 |
| $\{M_{BC,R}\}_j$ | 63.73 | 63.73 | 63.73 | 64.28 | 64.27 | 64.27 |
| $\{M_{C,U}\}_j$ | 81.95 | 81.93 | 81.94 | 83.07 | 83.01 | 83.04 |
| $\{M_{C,R}\}_j$ | 77.24 | 77.24 | 77.24 | 79.93 | 79.93 | 79.93 |
| $\{M_{Hw,Lw}\}_j$ | 67.77 | 67.71 | 67.74 | 70.06 | 70.03 | 70.05 |

TABLE 16

Leave-one-out validation results for classifying patients using DNN models.

| Soft-max ANN models | Cough features only | | | Cough plus simple clinical features | | |
|---|---|---|---|---|---|---|
| | Sensitivity | Specificity | Accuracy | Sensitivity | Specificity | Accuracy |
| Performance before Fine-tuning DNN models | | | | | | |
| $S_{Bo}$ | 81.19 | 84.23 | 83.72 | 85.15 | 85.23 | 85.22 |
| $S_C$ | 80.70 | 82.57 | 82.39 | 84.21 | 85.69 | 85.55 |
| $S_A$ | 65.81 | 66.58 | 66.28 | 66.67 | 66.85 | 66.78 |
| $S_P$ | 63.93 | 68.54 | 67.61 | 66.39 | 66.67 | 66.61 |
| $S_{LRTD}$ | 69.11 | 70.91 | 69.44 | 73.58 | 73.64 | 73.59 |
| $S_U$ | 75.47 | 75.59 | 75.58 | 71.70 | 75.77 | 75.42 |
| Performance after Fine-tuning DNN models | | | | | | |
| $S_{Bo}$ | 91.09 | 91.82 | 91.69 | 96.04 | 96.41 | 96.35 |
| $S_C$ | 91.23 | 92.66 | 92.52 | 98.25 | 98.35 | 98.34 |
| $S_A$ | 77.35 | 77.45 | 77.41 | 90.17 | 90.49 | 90.37 |
| $S_P$ | 71.31 | 71.46 | 71.43 | 86.07 | 86.67 | 86.54 |
| $S_{LRTD}$ | 86.18 | 86.36 | 86.21 | 92.68 | 92.73 | 92.69 |
| $S_U$ | 84.91 | 85.06 | 85.05 | 86.79 | 89.25 | 89.04 |

BIBLIOGRAPHY

The following documents are hereby incorporated in their entireties by reference.
1. Abeyratne, U. R., et al., *Cough sound analysis can rapidly diagnose childhood pneumonia*. Annals of biomedical engineering, 2013. 41(11): p. 2448-2462.
2. Kosasih, K., et al., *Wavelet augmented cough analysis for rapid childhood pneumonia diagnosis*. IEEE Transactions on Biomedical Engineering, 2015. 62(4): p. 1185-1194.
3. Abeyratne, U. *Blind reconstruction of non-minimum-phase systems from 1-D oblique slices of bispectrum*. 1999. IET.
4. Hinton G E, Salakhutdinov R R. Reducing the dimensionality of data with neural networks. science. 2006 Jul. 28; 313(5786):504-7.

In compliance with the statute, the invention has been described in language more or less specific to structural or methodical features. The term "comprises" and its variations, such as "comprising" and "comprised of" is used throughout in an inclusive sense and not to the exclusion of any additional features. It is to be understood that the invention is not limited to specific features shown or described since the means herein described herein comprises preferred forms of putting the invention into effect. The invention is, therefore, claimed in any of its forms or modifications within the proper scope of the appended claims appropriately interpreted by those skilled in the art.

Throughout the specification and claims (if present), unless the context requires otherwise, the term "substantially" or "about" will be understood to not be limited to the value for the range qualified by the terms.

Features, integers, characteristics, compounds, chemical moieties or groups described in conjunction with a particular aspect, embodiment or example of the invention are to be understood to be applicable to any other aspect, embodiment or example described herein unless incompatible therewith.

Any embodiment of the invention is meant to be illustrative only and is not meant to be limiting to the invention. Therefore, it should be appreciated that various other changes and modifications can be made to any embodiment described without departing from the spirit and scope of the invention

The invention claimed is:

1. A method for diagnosing one or more diseases of the respiratory tract for a patient, the method comprising:
   processing cough sounds acquired from a patient to produce cough sound feature signals representing one or more cough sound features from the cough segments;
   obtaining one or more disease signatures based on the cough sound feature signals; and
   classifying the one or more disease signatures to deem the cough segments as indicative of one or more of said diseases;
   wherein the obtaining of the one or more disease signatures based on the cough sound feature signals includes applying the cough sound features to each of a plurality of pre-trained disease signature decision machines, at least one of the pre-trained disease signature decision machines having been pre-trained to classify the cough sound features as corresponding to either a particular disease or to a non-disease state, and at least one other of the pre-trained disease signature decision machines having been pre-trained to classify the cough sound features as corresponding to a first particular disease or a second particular disease different from the first particular disease,
   wherein a plurality of disease signatures are obtained, each said disease signature being generated as a respective axis having values varying continuously between 0 and 1 and defining a respective space for distinguishing between two different diagnoses,
   wherein a response is provided for the patient along each of the axes, and
   wherein the responses for the axes are provided for the classifying.

2. The method according to claim 1, wherein the disease signature decision machines each comprise a trained Logistic Regression Model (LRM).

3. The method according to claim 2, wherein each trained Logistic Regression Model (LRM) is trained using a reduced set of training features being features determined to be significant to the LRM to thereby avoid overtraining of the LRM.

4. The method according to claim 3, wherein the training features are determined to be significant to the LRM by computing mean p-values for all training features and then selecting the features with mean p-values less than a threshold $P_{min}$.

5. The method according to claim 4, wherein independent variables for each LRM are values of the cough sound features and the output value from the LRM comprises a first prediction probability of the cough indicating the first particular disease with reference to the second particular disease for the at least one other of the pre-trained disease signature decision machines having been pre-trained to classify the cough sound features, and a second prediction probability with reference to the non-disease state for the at least one of the pre-trained disease signature decision machines having been pre-trained to classify the cough sound features as corresponding to either a particular disease or to a non-disease state.

6. The method according to claim 1, wherein one or more of the plurality of pre-trained signature decision machines include one or more trained neural networks.

7. The method according to claim 1, further comprising applying clinical patient measurements, in addition to the cough features, as independent variables to the disease signature decision machines.

8. The method according to claim 1, wherein the classifying of the one or more disease signatures to deem the cough segments as indicative of one or more of said diseases includes applying the disease signatures to a single classifier that is trained to cover all disease groups.

9. The method according to claim 1, wherein the classifying of the one or more disease signatures to deem the cough segments as indicative of one or more of said diseases includes applying the one or more disease signatures to a multiplicity of classifiers that are each trained to recognize a disease of interest.

10. The method according to claim 6, wherein the classifying of the one or more disease signatures includes classifying the one or more disease signatures as one of the following diseases: Bronchiolitis ($S_{Bo}$); Croup ($S_C$); Asthma/RAD ($S_A$); Pneumonia ($S_P$); Lower respiratory tract diseases ($S_{LRTD}$); Primary URTI ($S_U$).

11. The method according to claim 9, wherein d disease signatures are produced by the obtaining of the one or more disease signatures based on the cough sound feature signals and correspondingly the Artificial Neural Network (ANN) has a d-dimensional input layer with one input neuron corresponding to each of the disease signatures.

12. The method according to claim 11, wherein the ANN has a k-dimensional output layer wherein each neuron in the output layer outputs a probability corresponding to a disease.

13. The method according to claim 1, wherein the classifying of the one or more disease signatures includes compiling a compound effective probability measure $P_Q'$ as:

$$P_Q' = P_Q(1 - P_Z)$$

where $P_Q$ comprises an indicator of the probability of the patient belonging to disease Q and $P_z$ to disease Z whereby the product $P_Q(1-P_Z)$ indicates the probability of the compound event that the patient belongs to disease Q AND does not belong to disease Z.

14. The method according to claim 10, further comprising computing a cough index for each of a plurality of target diseases, wherein the cough index of a patient for a given target disease is computed as the ratio of coughs of the patient classified as indicative of the given target disease to the total number of coughs analyzed for said patient.

15. The method according to claim 1, further comprising applying one or more post screening tests to classifications from classifying of the one or more disease signatures to detect dominant false positives.

16. The method according to claim 15, further comprising adjusting the classifying of the one or more disease signatures based on the detected false positives.

17. The method according to claim 1, further comprising applying specific therapy to the patient based upon the particular disease diagnosed.

18. The method according to claim 1, wherein at least some of the axes embed domain-specific knowledge, and
wherein a proper subset of signatures are used in the classifying, based on a disease group being diagnosed.

19. A method for diagnosing one or more diseases of the respiratory tract for a patient, the method comprising:
acquiring cough sounds from the patient;
processing the cough sounds to produce cough sound feature signals representing one or more cough sound features from the cough segments;
obtaining one or more disease signatures based on the cough sound feature signals;
classifying the one or more disease signatures to deem the cough segments as indicative of one or more of said diseases; and
applying one or more post screening tests to classifications from classifying of the one or more disease signatures to detect dominant false positives,
wherein the obtaining of the one or more disease signatures based on the cough sound feature signals includes applying the cough sound features to each of one or more pre-trained disease signature decision machines, each said decision machine having been pre-trained to classify the cough sound features as corresponding to either a particular disease or to a non-disease state as corresponding to first particular disease or a second particular disease different from the first particular disease, and
wherein the one or more disease signature decision machines each comprise a trained Logistic Regression Model (LRM).

20. The method according to claim 19, wherein each trained LRM is trained using a reduced set of training features being features determined to be significant to the LRM to thereby avoid overtraining of the LRM.

21. The method according to claim 20, wherein the training features are determined to be significant to the LRM by computing mean p-values for all training features and then selecting the features with mean p-values less than a threshold $P_{min}$.

22. The method according to claim 21, wherein independent variables for each LRM are values of the cough sound features and the output value from the LRM comprises a first prediction probability of the cough indicating the first particular disease with reference to the second particular disease for the at least one other of the pre-trained disease signature decision machines having been pre-trained to classify the cough sound features, and a second prediction probability with reference to the non-disease state for the at least one of the pre-trained disease signature decision machines having been pre-trained to classify the cough sound features as corresponding to either a particular disease or to a non-disease state.

23. The method according to claim 19, further comprising applying clinical patient measurements, in addition to the cough features, as independent variables to the disease signature decision machines.

24. The method according to claim 19, wherein the classifying of the one or more disease signatures to deem the cough segments as indicative of one or more of said diseases includes applying the disease signatures to a single classifier that is trained to cover all disease groups.

25. The method according to claim 19, wherein the classifying of the one or more disease signatures to deem the cough segments as indicative of one or more of said diseases includes applying the one or more disease signatures to a multiplicity of classifiers that are each trained to recognize a disease of interest.

26. The method according to claim 19, wherein the classifying of the one or more disease signatures includes classifying the one or more disease signatures as one of the following diseases: Bronchiolitis ($S_{Bo}$); Croup ($S_C$); Asthma/RAD ($S_A$); Pneumonia ($S_P$); Lower respiratory tract diseases ($S_{LRTD}$); Primary URTI ($S_U$).

27. The method according to claim 19, further comprising adjusting the classifying of the one or more disease signatures based on the detected false positives.

28. The method according to claim 19, further comprising applying specific therapy to the patient based upon the particular disease diagnosed.

* * * * *